US008766037B2

(12) United States Patent
Lopato et al.

(10) Patent No.: US 8,766,037 B2
(45) Date of Patent: Jul. 1, 2014

(54) **DROUGHT RESPONSIVE EXPRESSION OF GENES FROM THE *ZEA MAYS RAB17* PROMOTER**

(75) Inventors: Sergiy Lopato, Morphett Vale (AU); Sarah Morran, Northfield (AU); Omid Eini, Kensington (AU); Peter Langridge, Teringie (AU)

(73) Assignee: Australian Centre for Plant Functional Genomics Pty Ltd, Urrbrae (AU)

( * ) Notice: Subject to any disclaimer, the term of this patent is extended or adjusted under 35 U.S.C. 154(b) by 96 days.

(21) Appl. No.: 13/265,819

(22) PCT Filed: Apr. 23, 2010

(86) PCT No.: PCT/AU2010/000460
§ 371 (c)(1),
(2), (4) Date: Jan. 10, 2012

(87) PCT Pub. No.: WO2010/121316
PCT Pub. Date: Oct. 28, 2010

(65) Prior Publication Data
US 2012/0102592 A1    Apr. 26, 2012

(30) Foreign Application Priority Data

Apr. 24, 2009  (AU) .............................. 2009901749

(51) Int. Cl.
*C12N 15/00*    (2006.01)
*C12N 15/113*   (2010.01)
*C12N 15/09*    (2006.01)

(52) U.S. Cl.
USPC ........ 800/289; 800/298; 800/320.3; 435/468; 435/419; 435/320.1; 536/23.1; 536/23.6; 536/24.1

(58) Field of Classification Search
None
See application file for complete search history.

(56) References Cited

U.S. PATENT DOCUMENTS

| 7,253,000 B2 * | 8/2007 | Sivasankar et al. ........... 435/468 |
| 7,491,813 B2 | 2/2009 | Wu et al. |
| 2007/0130645 A1 * | 6/2007 | Wu et al. ....................... 800/278 |

FOREIGN PATENT DOCUMENTS

| WO | WO 2005/103075 | 11/2005 |
| WO | WO 2006/060376 | 6/2006 |

OTHER PUBLICATIONS

Kennell. Principles and practices of nucleic acid hybridization. Progress in Nucleic Acid Research and Molecular Biology. 1971. 11: 259-301.*
Agarwal et al. Role of DREB transcription factors in abiotic and biotic stress tolerance in plants. Plant Cell Rep. 2006. 25: 1263-1274.*
Morran et al. Generation of drought-resistant transgenic cereals using transcription factors isolated from wheat grain. 11th International Wheat Genetics Symposium. Brisbane, Australia. Aug. 24-29, 2008. pp. 1-3.*
Lopato et al. GenBank Direct Submission of DQ353852, DQ353853, ABC86563, and ABC86564. Published Mar. 7, 2006.*
Clontech. GenomeWalker Universal Kit User Manual. Clontech Laboratories. 2007. pp. 1-30.*
Extended European Search Report for EP Patent Application No. 10766509.3 dated Oct. 24, 2012, 5 pages.
Morran et al., "Improvement of stress tolerance of wheat and barley by modulation of expression of DREB/CBF factors," *Plant Biotechnology Journal*, 9: 230-249, 2011.
Vilardell et al., "Gene sequence, developmental expression, and protein phosphorylation of RAB-17 in maize," *Plant Molecular Biology*, 14: 423-432, 1990.
Vilardell et al., "Regulation of the maize *rab17* gene promoter in transgenic heterologous systems," *Plant Molecular Biology*, 17(5): 985-993, 1991.

* cited by examiner

*Primary Examiner* — Cathy Kingdon Worley
*Assistant Examiner* — Ashley K Buran
(74) *Attorney, Agent, or Firm* — Klarquist Sparkman, LLP

(57) ABSTRACT

The present invention relates generally to the drought-specific expression of a nucleotide sequence of interest in one or more cells of a plant. In some particular embodiments, the present invention relates to the drought-specific expression of a nucleotide sequence of interest in wheat under the control of a Rab17 transcriptional control sequence.

12 Claims, 22 Drawing Sheets

FIGURE 4
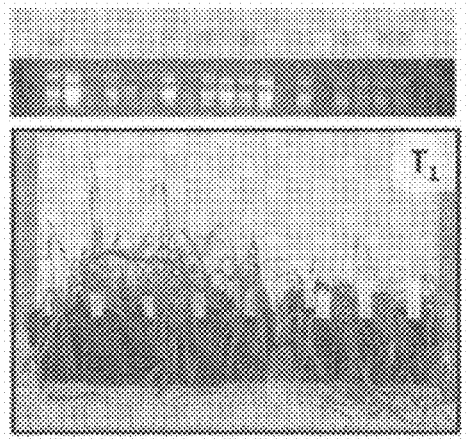
2X35S-TaDREB2, Line 1    Control
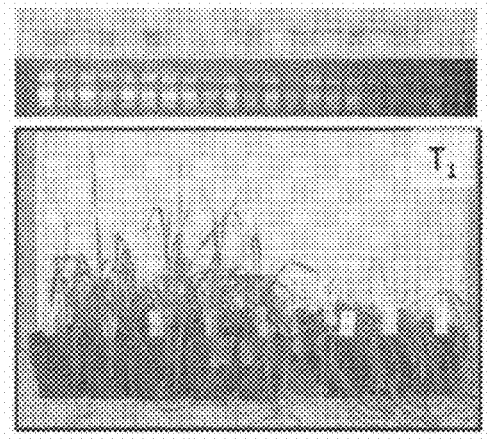
2X35S-TaDREB2, Line 5    Control
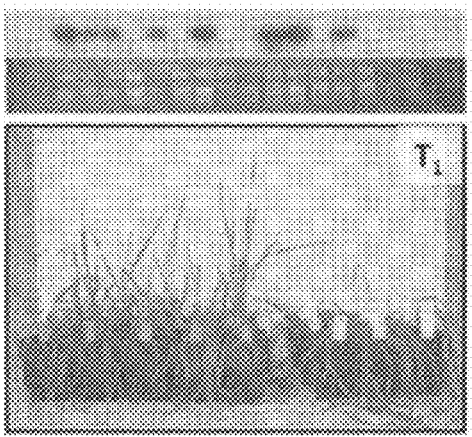
2X35S-TaDREB3, Line 7    Control
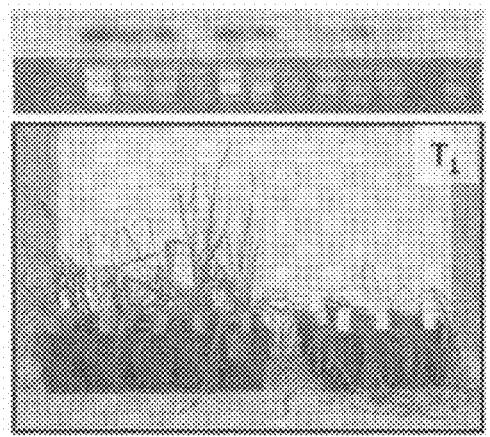
2X35S-TaDREB3, Line 12    Control FIGURE 3
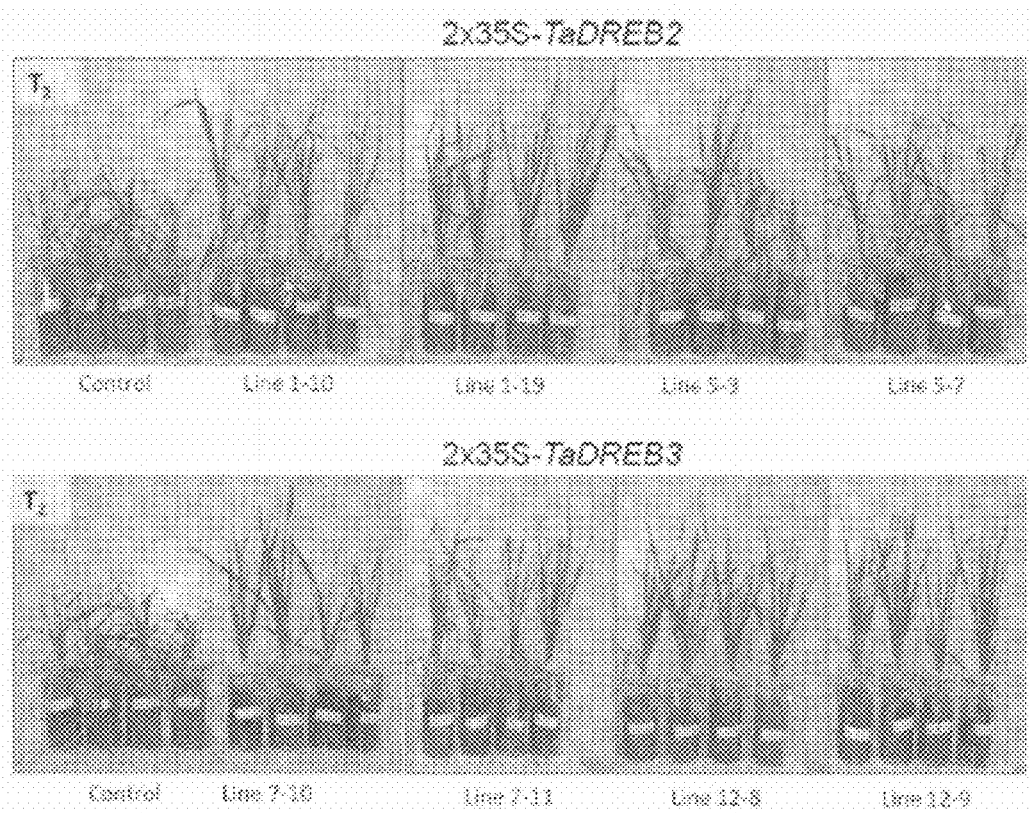
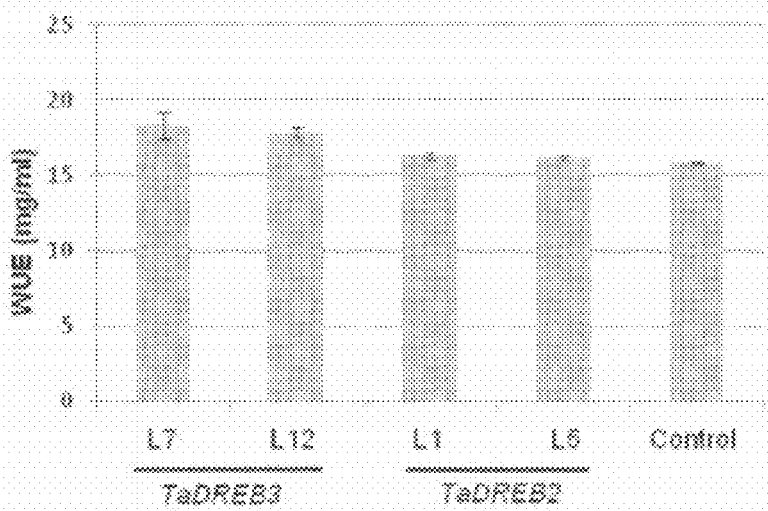

FIGURE 13
pRAB17-TaDREB2, T₁, drought tolerance, barley, Exp.N1
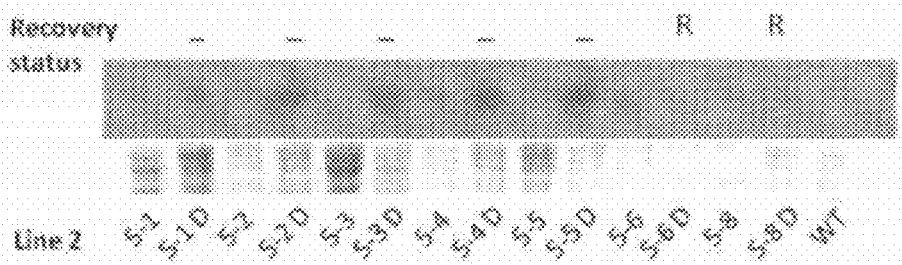
pRAB17-TaDREB3, T₂, drought tolerance, barley, Exp.N1
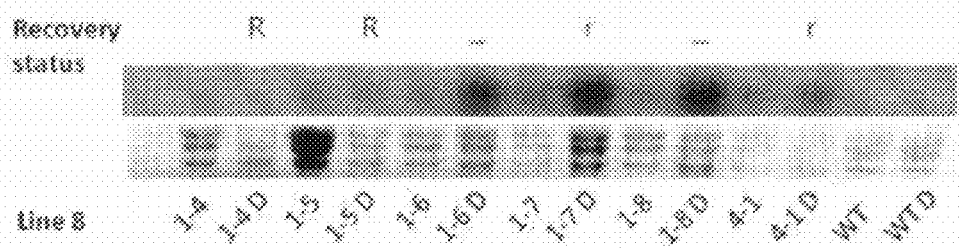
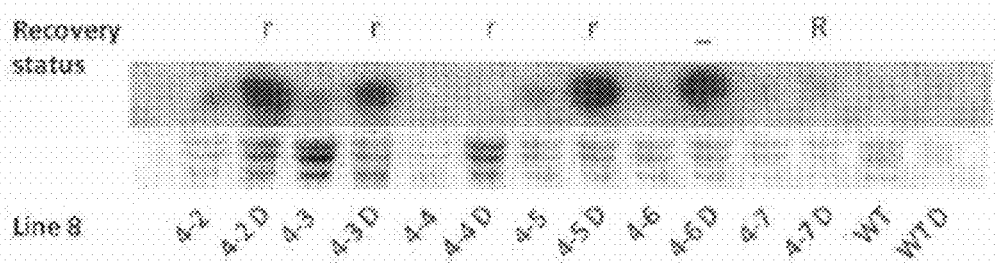

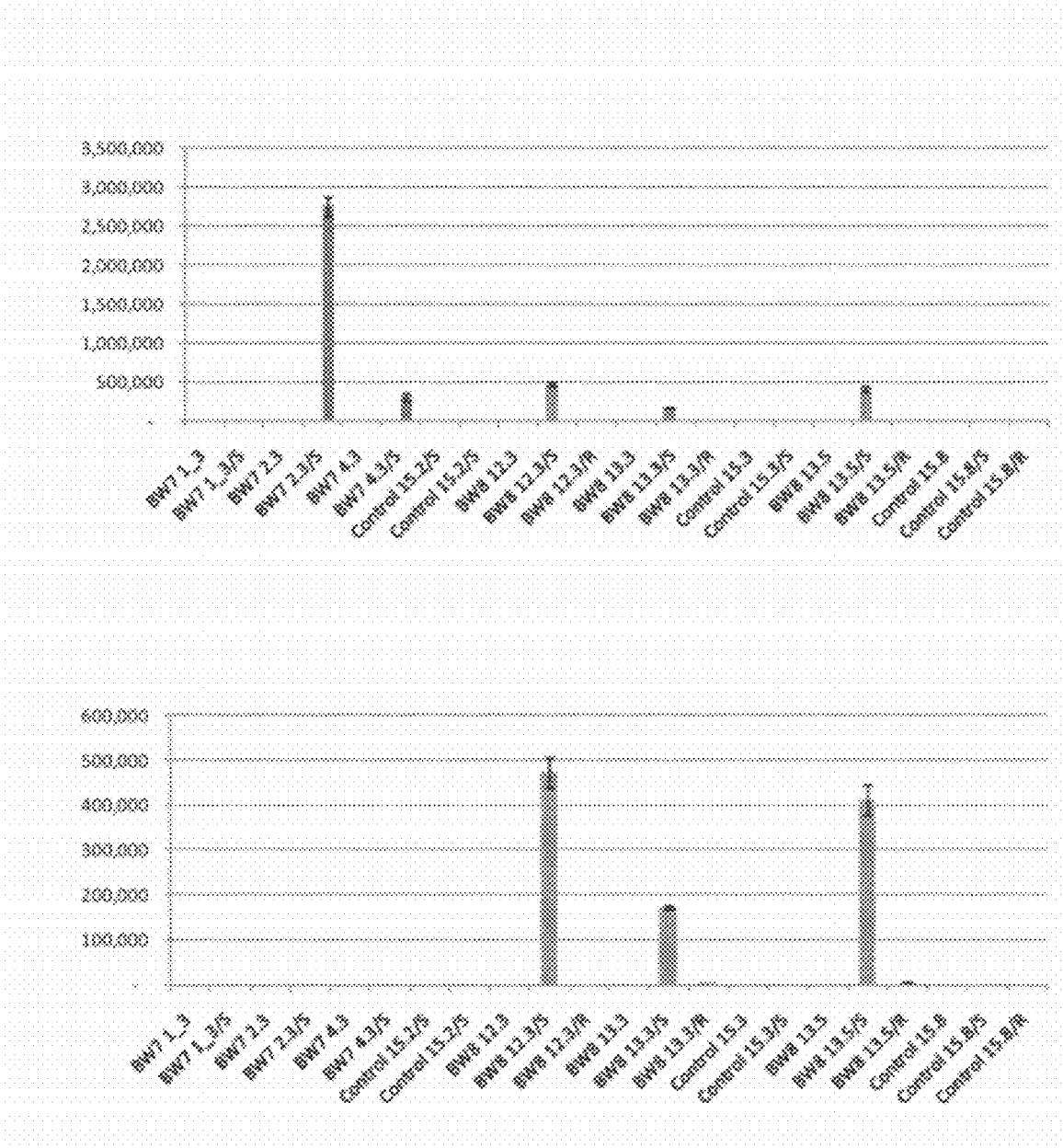

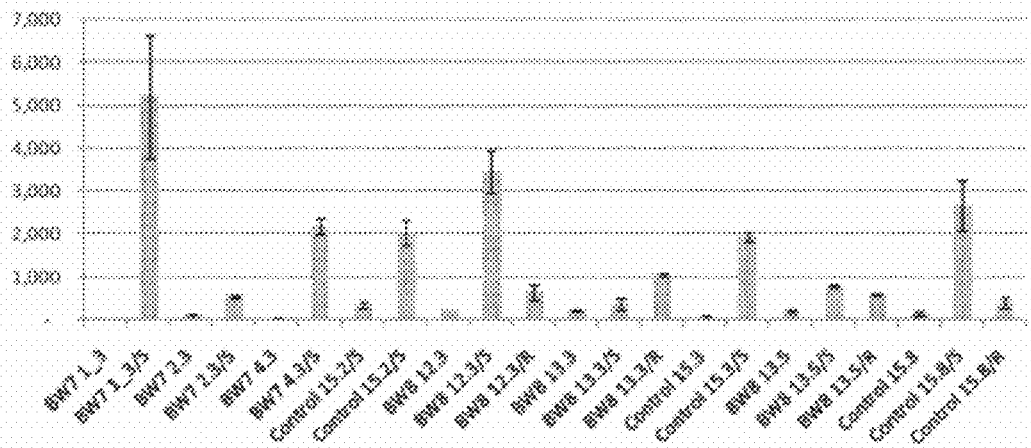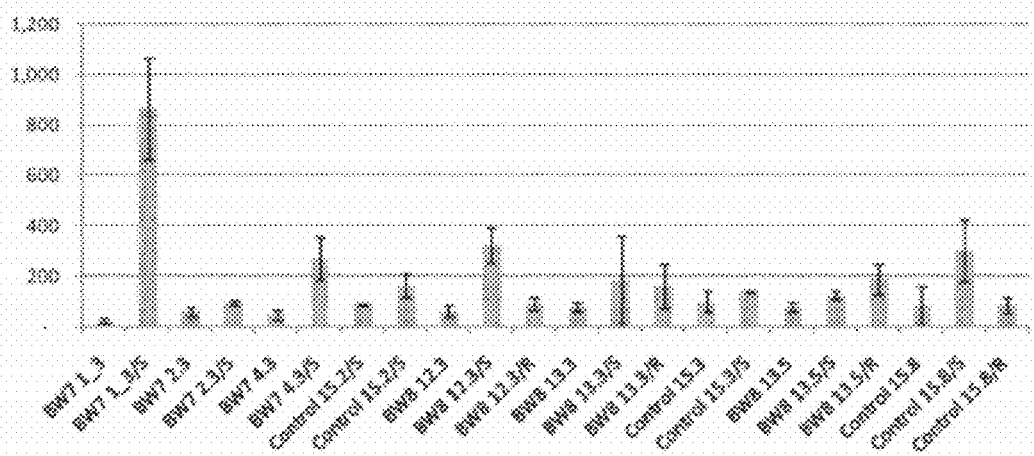

DROUGHT RESPONSIVE EXPRESSION OF GENES FROM THE *ZEA MAYS RAB17* PROMOTER

PRIORITY CLAIM

This is the U.S. National Stage of International Application No. PCT/AU2010/000460, filed Apr. 23, 2010, which was published in English under PCT Article 21(2), and which in turn claims priority from Australian provisional patent application 2009901749, filed Apr. 24, 2009, the contents of which are incorporated herein by reference in their entirety.

FIELD

The present invention relates generally to the drought-specific expression of a nucleotide sequence of interest in one or more cells of a plant.

A Sequence Listing is submitted herewith as an ASCII compliant text file named "Sequence_Listing.txt", created on Jan. 22, 2014, and having a size of ~1.32 kilobytes, as permitted under 37 CFR 1.821(c). The material in the aforementioned file is hereby incorporated by reference in its entirety.

BACKGROUND

Several families of transcription factors, such as DREB/CBF, ERF, MYK, MYB, AREB/ABF, NAC and HDZip class I and II, have been shown to be involved in the regulation of drought response in plants. These factors bind specific cis-elements on the promoters of drought regulated genes.

The dehydration-responsive element-binding proteins (DREBs) or C-repeat-binding proteins (CBFs) are among the first discovered families of transcription factors responsible for gene regulation under conditions of water deficiency. It is a group of transcriptional factors with a single AP2 domain, which controls the expression of many stress inducible genes in plants. Many DREB/CBF factors are themselves induced by such abiotic stresses, like drought, cold, salinity, and heat.

Six DREB transcription factors, including four DREB1/CBF and two DREB2 factors have been identified in *Arabidopsis*. It has been demonstrated that DREB1/CBF factors are induced by drought, salt and cold, whereas DREB2 factors are induced by drought and salt only.

Since discovery of the role of DREB/CBF factors in the stress response, several attempts have been undertaken to demonstrate their potential to improve stress tolerance in *Arabidopsis*, and crop plants such as *Brassica junceae*, soybean, rice, wheat and other grasses.

In the majority of attempts to overexpress DREB factors in plants, constitutive promoters such as the Cauliflower mosaic virus $^{35}$S promoter, rice actin 1 promoter and maize polyubiquitin promoter have been used. However, in most cases strong constitutive expression led to different degrees of growth retardation, which subsequently led to dwarfism of the transgenic plants.

There have been attempts to overcome the problems of severe growth retardation by reducing the duration of overexpression using stress inducible promoters. For example expression of DREB factors under the control of the rd29A promoter has been attempted in a range of plants. However, this promoter was generally observed to have some level of basal expression in the absence of drought stress. As mentioned above, expression of DREB factors in the absence of drought stress is associated with the dwarfism and or stunting of plants.

In light of the above, it would be desirable to be able to drive the expression of nucleotide sequences, including those involved in drought tolerance (such as DREB factors), in a drought responsive manner. In this way, the nucleotide sequences could be expressed when required, ie. in response to drought, but not be expressed in the absence of drought where undesirable phenotypes such as dwarfism and or stunting of plants may occur.

Reference to any prior art in this specification is not, and should not be taken as, an acknowledgment or any form of suggestion that this prior art forms part of the common general knowledge in any country.

SUMMARY

In a first aspect, the present invention provides a method for effecting drought responsive expression of a nucleotide sequence of interest in one or more cells of a plant, the method comprising expressing in the one or more cells of the plant the nucleotide sequence of interest operably connected to a transcriptional control sequence which is drought inducible in the plant and has substantially no basal activity in the plant in the absence of drought.

In some embodiments, the plant is a wheat plant.

In some embodiments, the transcriptional control sequence comprises a Rab17 transcriptional control sequence. In some embodiments, the Rab17 transcriptional control sequence used in accordance with the present invention may be a *Zea mays* Rab17 transcriptional control sequence or a functionally active fragment or variant thereof.

In some embodiments, the nucleotide sequence of interest comprises a nucleotide sequence which, when expressed by one or more cells of a plant, improves the drought tolerance of the plant. In some embodiments, the nucleotide sequence of interest encodes a DREB polypeptide.

In a second aspect, the present invention also provides a nucleic acid construct comprising a nucleotide sequence of interest operably connected to a drought inducible transcriptional control sequence which has substantially no basal activity in a plant in the absence of drought.

In some embodiments, the transcriptional control sequence is drought inducible in wheat and has substantially no basal activity in wheat in the absence of drought. In some embodiments, the transcriptional control sequence comprises a Rab17 transcriptional control sequence. In some embodiments, the transcriptional control sequence comprises a *Zea mays* Rab17 transcriptional control sequence or a functionally active fragment or variant thereof.

In some embodiments, the nucleotide sequence of interest comprises a nucleotide sequence which, when expressed by one or more cells of a plant, improves the drought tolerance of the plant. In some embodiments, the nucleotide sequence of interest encodes a DREB polypeptide.

In a third aspect, the present invention provides a genetically modified cell comprising a nucleic acid construct of the second aspect of the invention or a genomically integrated form thereof.

In some embodiments, the cell is a wheat cell.

In a fourth aspect, the present invention contemplates a multicellular structure comprising one or more cells of the third aspect of the invention.

In some embodiments, the multicellular structure comprises a plant or a part, organ or tissue thereof. In some embodiments, the plant or a part, organ or tissue thereof comprises a wheat plant or a part, organ or tissue thereof.

In some embodiments, the present invention also provides a plant or a part, organ or tissue thereof having improved drought tolerance, wherein the plant comprises one or more cells of the third aspect of the invention.

Nucleotide and amino acid sequences are referred to herein by a sequence identifier number (SEQ ID NO:). A summary of the sequence identifiers is provided in Table 1. A sequence listing is provided at the end of the specification.

TABLE 1

Summary of Sequence Identifiers

| Sequence Identifier | Sequence | Sequence Listing Number |
| --- | --- | --- |
| SEQ ID NO: 1 | Zea mays Rab17 promoter | 400 <1> |

DESCRIPTION OF EXEMPLARY EMBODIMENTS

It is to be understood that the following description is for the purpose of describing particular embodiments only and is not intended to be limiting with respect to the above description.

In a first aspect, the present invention provides a method for effecting drought responsive expression of a nucleotide sequence of interest in one or more cells of a plant, the method comprising expressing in the one or more cells of the plant the nucleotide sequence of interest operably connected to a transcriptional control sequence which is drought inducible in the plant and has substantially no basal activity in the plant in the absence of drought.

Reference herein to a plant may include seed plant species such as monocotyledonous angiosperm plants ("monocots"), dicotyledonous angiosperm plants ("dicots") and/or gymnosperm plants.

In some embodiments, the plant is a cereal crop plant. As used herein, the term "cereal crop plant" may be a member of the Poaceae (grass family) that produces grain. Examples of Poaceae cereal crop plants include wheat, rice, maize, millets, sorghum, rye, triticale, oats, barley, teff, wild rice, spelt and the like. The term cereal crop plant should also be understood to include a number of non-Poaceae plant species that also produce edible grain, which are known as the pseudocereals and include, for example, amaranth, buckwheat and quinoa.

In some embodiments, the plant is a wheat plant. As referred to herein, "wheat" should be understood as a plant of the genus *Triticum*. Thus, the term "wheat" encompasses diploid wheat, tetraploid wheat and hexaploid wheat. In some embodiments, the wheat plant may be a cultivated species of wheat including, for example, *T. aestivum, T. durum, T. monococcum* or *T. spelta*. In some embodiments, the term "wheat" refers to wheat of the species *Triticum aestivum*.

As set out above, the method contemplates effecting drought-responsive expression of a nucleotide sequence of interest in one or more cells of a plant.

"Drought responsive expression", as referred to herein, should be understood to refer to the transcription of a nucleotide sequence in one or more cells of the plant when the plant experiences drought and substantially no detectable transcription of the nucleotide sequence of interest in the one or more cells of the plant when the plant does not experience drought.

"Drought" as referred to herein should be understood to include any situation wherein the amount of water available to a plant, at a physiologically appropriate level of salinity, is less than the optimum level of water for that plant. In some embodiments, drought may include a low volumetric water content (VWC) in a soil. In some embodiments, drought may include a soil VWC of less than 10%, less than 7%, less than 5%, less than 4% or less than 3%. In some embodiments, drought may also include other forms of osmotic stress such as wherein a relatively high volume of water is available, but the level of salinity in the water is sufficiently high to cause osmotic stress in the plant. In some embodiments, reference herein to "drought" includes conditions of sufficient severity to cause visible symptoms in a plant such as loss of turgor, wilting, rolled leaves, chlorosis, growth retardation and/or death of a plant.

In the method of the present invention drought responsive expression of the nucleotide sequence of interest is effected by the nucleotide sequence of interest being operably connected to a transcriptional control sequence which is drought inducible in the plant and has substantially no basal activity in the plant in the absence of drought.

As used herein, the term "transcriptional control sequence" should be understood as a nucleotide sequence that modulates at least the transcription of an operably connected nucleotide sequence. As such, the transcriptional control sequences of the present invention may comprise any one or more of, for example, a promoter, 5' or 3' UTR, enhancer or upstream activating sequence. In some embodiments, the transcriptional control sequence may comprise a promoter and/or a 5' UTR.

As used herein, the term "operably connected" refers to the connection of a transcriptional control sequence, such as a promoter, and a nucleotide sequence of interest in such a way as to bring the nucleotide sequence of interest under the transcriptional control of the transcriptional control sequence. For example, promoters are generally positioned 5' (upstream) of a nucleotide sequence to be operably connected to the promoter.

As set out above, the transcriptional control sequences contemplated for use in the present invention are "drought inducible". Drought inducible transcriptional control sequences should be understood to include transcriptional control sequences which generate a higher rate and/or higher level of transcription of an operably connected nucleotide sequence in a plant when the plant is exposed to drought. In some embodiments, the drought inducible transcriptional control sequence may be activated by one or more transcription factors or other polypeptides which are expressed in a plant when the plant is exposed to drought.

The transcriptional control sequences contemplated for use in the present invention also comprise "substantially no basal activity in the absence of drought". As referred to herein, this should be understood to mean that the transcriptional control sequence has no detectable expression in a plant of interest in the absence of drought. In some embodiments, "no detectable expression" should be understood to mean that no transcription of an operably connected nucleotide sequence can be detected by Northern blotting and/or Q-PCR. As will be appreciated, some very low level of expression which is not detectable by Northern blotting and/or Q-PCR may still exist in transcriptional control sequences that fall within the meaning of "substantially no basal activity" as used herein.

Furthermore, the terms "drought inducible" and "substantially no basal activity in the absence of drought" are to be assessed in the context of a plant of interest. For example a particular transcriptional control sequence may exhibit drought inducibility and substantially no basal activity in the absence of drought in a plant of interest, but need not exhibit both or either of these characteristics in all plant species to fall within the meaning of the above-referenced terms for the purposes of the present invention. In some embodiments, the terms "drought inducible" and "substantially no basal activity in the absence of drought" may also be assessed in the context of a particular tissue type. For example, a particular transcriptional control sequence may exhibit drought inducibility and substantially no basal activity in the absence of drought in a particular plant tissue of interest, eg. the leaves, but need not exhibit both or either of these characteristics in all plant tissues to fall within the meaning of the above-referenced terms for the purposes of the present invention.

In some embodiments, the transcriptional control sequence comprises a Rab17 transcriptional control sequence.

As referred to herein, the term "Rab17 transcriptional control sequence" refers to any transcriptional control sequence which is derived from a Rab17 gene in a plant.

The Rab17 gene may also be known by other names including, for example, dehydrin1, dhn1 or lea2. An example of a Rab17 gene is the *Zea mays* Rab17 gene described under Entrez Gene GeneID: 542373.

The Rab17 gene from *Zea mays* is induced by ABA and water deficit. It has sequence similarity to a major group of the late embryogenesis-abundant proteins. The members of this subfamily of proteins are constitutively expressed in mature embryos and, in some cases, in endosperm, and can be activated in the rest of plant tissues by several forms of osmotic stress such as water, salt and cold stress. Genes similar to the maize Rab17 have been isolated from some other plants and promoter activity of some of them has been tested. The product of the maize Rab17 gene can bind the nuclear localisation signal (NLS) sequence and this binding is dependent upon phosphorylation with protein kinase CK2.

Rab17 homologs have also been identified in a number of other plant species, and the term "Rab17 gene" as used herein should be understood to encompass all such homologs.

In some embodiments, reference herein to a "Rab17 gene" may include genes which encode a polypeptide comprising at least 50%, at least 55%, at least 60%, at least 65%, at least 70%, at least 75%, at least 80%, at least 85%, at least 90%, at least 91%, at least 92%, at least 93%, at least 94%, at least 95% at least 96%, at least 97%, at least 98%, at least 99% or 100% sequence identity to the *Zea mays* Rab17 polypeptide as set forth in Entrez protein accession number NP_001105419.

When comparing amino acid sequences to calculate a percentage identity, the compared sequences should be compared over a comparison window of at least 50 amino acid residues, at least 100 amino acid residues, at least 150 amino acid residues, or over the full length of NP_001105419. The comparison window may comprise additions or deletions (ie. gaps) of about 20% or less as compared to the reference sequence (which does not comprise additions or deletions) for optimal alignment of the two sequences. Optimal alignment of sequences for aligning a comparison window may be conducted by computerised implementations of algorithms such as the BLAST family of programs as, for example, disclosed by Altschul et al. (*Nucl. Acids Res.* 25: 3389-3402, 1997). A detailed discussion of sequence analysis can be found in Unit 19.3 of Ausubel et al. ("Current Protocols in Molecular Biology" John Wiley & Sons Inc, 1994-1998, Chapter 15, 1998).

In some embodiments, reference herein to a "Rab17 gene" may include genes which encode an mRNA comprising at least 50%, at least 55%, at least 60%, at least 65%, at least 70%, at least 75%, at least 80%, at least 85%, at least 90%, at least 91%, at least 92%, at least 93%, at least 94%, at least 95% at least 96%, at least 97%, at least 98%, at least 99% or 100% sequence identity to the *Zea mays* Rab17 mRNA as set forth in Entrez nucleotide accession number NM_001111949.

When comparing nucleotide sequences to calculate a percentage identity, the compared sequences should be compared over a comparison window of at least 100 nucleotide residues, at least 200 nucleotide residues, at least 400 nucleotide residues, at least 600 nucleotide residues or over the full length of NM_001111949. In some embodiments, the comparison window may comprise at least 100 nucleotide residues, at least 200 nucleotide residues, at least 400 nucleotide residues or over the full length of the CDS sequence in NM_001111949. The comparison window may comprise additions or deletions (ie. gaps) of about 20% or less as compared to the reference sequence (which does not comprise additions or deletions) for optimal alignment of the two sequences. Optimal alignment of sequences for aligning a comparison window may be conducted by computerised implementations of algorithms such as the BLAST family of programs as, for example, disclosed by Altschul et al. (*Nucl. Acids Res.* 25: 3389-3402, 1997). A detailed discussion of sequence analysis can be found in Unit 19.3 of Ausubel et al. ("Current Protocols in Molecular Biology" John Wiley & Sons Inc, 1994-1998, Chapter 15, 1998).

A Rab17 gene may also include a nucleotide sequence which hybridises to a nucleic acid comprising the nucleotide sequence set forth in Entrez nucleotide accession number NM_001111949 under stringent conditions.

As used herein, "stringent" hybridisation conditions will be those in which the salt concentration is less than about 1.5 M Na ion, typically about 0.01 to 1.0 M Na ion concentration (or other salts) at pH 7.0 to 8.3 and the temperature is at least 30° C. Stringent conditions may also be achieved with the addition of destabilising agents such as formamide. In some embodiments, stringent hybridisation conditions may be low stringency conditions, medium stringency conditions or high stringency conditions. Exemplary low stringency conditions include hybridisation with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridisation in 40 to 45% formamide, 1.0 M NaCl, 1% SDS at 37° C., and a wash in 0.5× to 1×SSC at 55 to 60° C. Exemplary high stringency conditions include hybridisation in 50% formamide, 1 M NaCl, 1% SDS at 37° C., and a wash in 0.1×SSC at 60 to 65° C. Optionally, wash buffers may comprise about 0.1% to about 1% SDS. Duration of hybridisation is generally less than about 24 hours, usually about 4 to about 12 hours.

Specificity of hybridisation is also a function of post-hybridisation washes, with the critical factors being the ionic strength and temperature of the final wash solution. For DNA-DNA hybrids, the thermal melting point ($T_m$) can be approximated from the equation of Meinkoth and Wahl (*Anal. Biochem.* 138: 267-284, 1984), ie. $T_m=81.5°$ C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridisation solution, and L is the length of the hybrid in base pairs. The $T_m$ is the temperature (under defined ionic strength and pH) at which 50% of a complementary target sequence hybridises to a perfectly matched probe. $T_m$ is reduced by about 1° C. for each 1% of mismatching; thus, $T_m$, hybridisation, and/or wash conditions can be adjusted to hybridise to sequences of different degrees of complementarity. For example, sequences with ≥90% identity can be hybridised by decreasing the $T_m$ by about 10°

C. Generally, stringent conditions are selected to be about 5° C. lower than the $T_m$ for the specific sequence and its complement at a defined ionic strength and pH. However, high stringency conditions can utilise a hybridisation and/or wash at, for example, 1, 2, 3, or 4° C. lower than the $T_m$; medium stringency conditions can utilise a hybridisation and/or wash at, for example, 6, 7, 8, 9, or 10° C. lower than the $T_m$; low stringency conditions can utilise a hybridisation and/or wash at, for example, 11, 12, 13, 14, 15, or 20° C. lower than the $T_m$. Using the equation, hybridisation and wash compositions, and desired $T_m$, those of ordinary skill will understand that variations in the stringency of hybridisation and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridisation of nucleic acids is found in Tijssen (*Laboratory Techniques in Biochemistry and Molecular Biology-Hybridisation with Nucleic Acid Probes*, Pt I, Chapter 2, Elsevier, N.Y., 1993), Ausubel et al., eds. (*Current Protocols in Molecular Biology*, Chapter 2, Greene Publishing and Wiley-Interscience, New York, 1995) and Sambrook et al. (*Molecular Cloning: A Laboratory Manual*, 2$^{nd}$ ed., Cold Spring Harbor Laboratory Press, Plainview, N.Y., 1989).

In some embodiments, examples of Rab17 genes include genes encoding the Rab17 mRNAs set forth in the table below:

TABLE 2

Examples of Rab17 genes

| Entrez Nucleotide accession number (mRNA) | Source organism |
|---|---|
| AJ606474 | *Fagus sylvatica* |
| X63061 | *Pisum sativum* |
| EU791889 | *Cichorium intybus* |
| NM_001111949 | *Zea mays* |
| X15288 | *Hordeum vulgare* |
| X15290 | *Zea mays* |
| AM180925 | *Aegilops umbellulata* |
| AJ844000 | *Plantago major* |
| DQ487106 | *Panax ginseng* |
| AM161646 | *Medicago saliva* |
| AY130998 | *Brassica juncea* |
| AY786415 | *Oryza saliva* |
| AY607705 | *Quercus robur* |
| AY303803 | *Brassica napus* |
| AJ300524 | *Populus euramericana* |
| AJ289610 | *Pinus sylvestris* |
| AF109916 | *Picea glauca* |
| AF159804 | *Vigna unguiculata* |
| AF181451 | *Hordeum vulgare* |
| Y15813 | *Solanum commersonii* |
| U11696 | *Sorghum bicolor* |
| X74067 | *Craterostigma plantagineum* |

As set out above, in some embodiments, the present invention contemplates transcriptional control sequences derived from a Rab17 gene.

The term "derived from", as used herein, refers to a source or origin for the transcriptional control sequence. For example, a transcriptional control sequence "derived from a Rab17 gene" refers to a transcriptional control sequence which, in its native state, is operably connected to a Rab17 gene.

The Rab17 transcriptional control sequences contemplated herein may be derived from any source, including isolated from any suitable organism or they may be synthetic nucleic acid molecules.

In some embodiments the Rab17 transcriptional control sequences contemplated herein are derived from a plant. In some embodiments, the transcriptional control sequences of the present invention are derived from a monocot plant species and in some embodiments, the transcriptional control sequences of the present invention are derived from a cereal crop plant species. In some embodiments, the transcriptional control sequence is derived from *Zea mays*.

Transcriptional control sequences may be isolated from Rab17 genes using techniques known in the art. Such techniques may be predicated on utilizing the sequence homology of the Rob 17 coding region. For example, all or part of the Rab17 coding region sequence may be used as a probe to hybridize with homologous sequences in a genomic DNA library of a chosen organism. Methods are readily available in the art for the hybridization of nucleic acid sequences. An extensive guide to the hybridization of nucleic acids is found in Tijssen, Laboratory Techniques in Biochemistry and Molecular Biology-Hybridization with Nucleic Acid Probes, Part I, Chapter 2 Overview of principles of hybridization and the strategy of nucleic acid probe assays", Elsevier, N.Y. (1993); and Current Protocols in Molecular Biology, Chapter 2, Ausubel, et al., Eds., Greene Publishing and Wiley-Interscience, New York (1995). Further exemplary methods for the isolation of promoters or other transcriptional control sequences from a plant gene, are described in WO 2007/092992, WO 2008/052285, WO2009/033229, WO 2007/137361 and 2007/048207. As will be appreciated a range of other in vitro and in silica methods for the identification of promoters associated with a particular plant gene, such as Rab17, would be readily ascertained by one of skill in the art.

Examples of Rab17 transcriptional control sequences include those described by Buchanan et al. (*Genetics* 168(3): 1639-1654, 2004).

In some embodiments, the Rab17 transcriptional control sequence used in accordance with the present invention may be a *Zea mays* Rab17 transcriptional control sequence or a functionally active fragment or variant thereof.

The *Zea mays* Rab17 promoter has been tested in several heterologous systems. Firstly, the promoter was tested in stably transformed tobacco and by transient expression of rice protoplasts and in both cases induction of the promoter by water stress and/or ABA treatment has been demonstrated. The activity of a 1.3 kb long promoter fragment of Rab17 fused to the GUS gene was analysed in transgenic wild type *Arabidopsis* plants, as well as in ABA-deficient and ABA-insensitive mutants of *Arabidopsis*. Although the Rab17 promoter was active in the embryo and endosperm during late seed development, during seed germination promoter activity decreased and GUS activity was not enhanced by ABA and water deficit in transgenic wild type and mutant plants. These data suggest that different molecular mechanisms mediate seed-specific expression and ABA and water stress induction of the Rab17 promoter, and demonstrate that the mechanism of stress induction is different in maize and *Arabidopsis*. Phylogenetic analysis of the 5'-noncoding regions from the Rab16/17 gene family of sorghum, maize and rice revealed the absence of some important cis-elements in the promoters and some differences in the expression of Rab17-like genes in these plants.

In some embodiments, the *Zea mays* Rab17 transcriptional control sequence or a functionally active fragment or variant thereof comprises the nucleotide sequence set forth in SEQ ID NO: 1 or a functionally active fragment or variant thereof.

Notwithstanding the above, the *Zea mays* Rab17 transcriptional control sequence has generally been observed to have a relatively high level of basal expression, ie. expression in the absence of drought, when expressed in heterologous plant species.

However, in accordance with the present invention, the *Zea mays* Rab17 transcriptional control sequence has been surprisingly identified to be drought inducible in wheat while also having substantially no basal activity in wheat in the absence of drought.

In addition, as described later, transgenic wheat plants which expressed DREB-encoding nucleotide sequences operably connected to the *Zea mays* Rab17 promoter also demonstrated no undesired developmental features like stunting growth, dwarfism, delayed flowering, and smaller spikes, which have been observed in plants with constitutive overexpression of DREB factors.

Thus, in some embodiments of the first aspect of the invention, the transcriptional control sequence comprises a *Zea mays* Rab17 transcriptional control sequence or a functionally active fragment or variant thereof, and the plant is a wheat plant as hereinbefore described.

"Functionally active fragments" or "Functionally active variants" of the *Zea mays* Rab17 transcriptional control sequence may include fragments or variants of a transcriptional control sequence which retain the functional activity of the *Zea mays* Rab17 transcriptional control sequence, as hereinbefore described. In some embodiments, the functionally active fragment or variant at least exhibits drought inducibility in wheat while also having substantially no basal activity in wheat in the absence of drought.

In some embodiments of the invention the functionally active fragment is at least 200 nucleotides (nt), at least 300 nt, at least 400 nt, at least 500 nt or at least 600 nt in length. In further embodiments, the fragment comprises at least 200 nt, at least 300 nt, at least 400 nt, at least 500 nt or at least 600 nt contiguous bases from the nucleotide sequence set forth in SEQ ID NO: 1.

"Functionally active variants" may include orthologous transcriptional control sequences from other organisms; mutants of the transcriptional control sequence; variants of the transcriptional control sequence wherein one or more of the nucleotides within the sequence has been substituted, added or deleted; and analogs that contain one or more modified bases or DNA or RNA backbones modified for stability or for other reasons.

As will be appreciated, functionally active fragments or variants of the *Zea mays* Rab17 transcriptional control sequence may include transcriptional control sequences isolated from other plants and/or synthetic nucleotide sequences.

In some embodiments, the functionally active fragment or variant comprises at least at least 50%, at least 55%, at least 60%, at least 65%, at least 70%, at least 75%, at least 80%, at least 85%, at least 90%, at least 91%, at least 92%, at least 93%, at least 94%, at least 95% at least 96%, at least 97%, at least 98%, at least 99% or 100% nucleotide sequence identity to the nucleotide sequence set forth in SEQ ID NO: 1. When comparing nucleic acid sequences to calculate a percentage identity, the compared nucleotide sequences should be compared over a comparison window of at least 200 nucleotides (nt), at least 300 nt, at least 400 nt, at least 500 nt, at least 600 nt or over the full length of SEQ ID NO: 1. The comparison window may comprise additions or deletions (ie. gaps) of about 20% or less as compared to the reference sequence (which does not comprise additions or deletions) for optimal alignment of the two sequences. Optimal alignment of sequences for aligning a comparison window may be conducted as hereinbefore described.

In some embodiments, the functionally active fragment or variant comprises a nucleic acid molecule which hybridises to a nucleic acid molecule defining a transcriptional control sequence of the present invention under stringent conditions. In some embodiments, the functionally active fragment or variant comprises a nucleic acid molecule which hybridises to a nucleic acid molecule comprising the nucleotide sequence set forth in SEQ ID NO: 1 under stringent conditions.

In some embodiments, "stringent conditions" may be as hereinbefore described.

The present invention may be used to effect drought specific expression of any nucleotide sequence of interest in one or more cells of a plant.

In some embodiments, the nucleotide sequence of interest comprises a nucleotide sequence which, when expressed by one or more cells of a plant, improves the drought tolerance of the plant.

"Drought tolerance" as referred to herein refers to any trait in the plant which allows the plant to survive, recover and/or reproduce during or after experiencing drought. Measures of drought tolerance may include, for example, the ability of a plant to continue to grow, reproduce or yield during or after an episode of drought; the rate or frequency of recovery of plants after an episode of drought; the extent of any yield penalty for a plant after experiencing an episode of drought; the water use efficiency of a plant; and the like. "Improvement" in the drought tolerance of a plant should be seen as any increase in the ability of a plant to survive, recover or reproduce during or after experiencing drought. For example, "improved" drought tolerance of a plant may include an increased ability of a plant to continue to grow, reproduce or yield during or after an episode of drought and/or at lower soil moisture; an increased rate or frequency of recovery of plants after an episode of drought; a decrease in or amelioration of any yield penalty associated with an episode of drought; increased water use efficiency of a plant; and the like.

Examples of "a nucleotide sequence which, when expressed by one or more cells of a plant, improves the drought tolerance of the plant" include, for example: genes encoding transcription factors such as DREB factors, MYC factors, MYB, factors, HDZip factors, bZip factors, HSE factors, ERF factors, WRKY factors, etc.; genes encoding protein kinases, which are activated or transcriptionally up-regulated under drought stress, such as SAPKs, receptor kinases, MAP kinases, and the like; genes encoding phosphatases related to stress responses such as ZmPP2C, type 1 inositol 5-phosphatase and the like; Stress inducible genes which protect cell integrity (eg. membrane stability, chloroplast/chlorophyll stability, correct protein folding and protein stability, and the like) such as LEA, DHNs, COR, RD and the like; genes encoding water channels such as aquaporins, PIPs, TIPs and NIPs; genes encoding stomata opening regulators such as AtMRP4, a guard cell plasma membrane ABCC-type ABC transporter, NFYA5 TF, NAC and MYB TFs and the like; genes responsible for sugar metabolism such as trehalose-6-phosphate synthase (TPS) and trehalose-6-phosphate phosphatase (TPP), ABA2 (or GLUCOSE INSENSITIVE 1 [GIN1]) encoding a short-chain dehydrogenase/reductase; genes delaying drought-induced leaf senescence such as senescence associated receptor protein kinase (SARK), a gene encoding a maturation/senescence-dependent receptor protein kinase.

In some embodiments, the nucleotide sequence of interest encodes a DREB polypeptide.

The dehydration-responsive element-binding proteins (DREBs) or C-repeat-binding proteins (CBFs) are among the first discovered families of transcription factors responsible for gene regulation under conditions of water deficiency.

In some embodiments, a "DREB polypeptide" as referred to herein, may comprise an AP2 domain. In some embodiments, the DREB polypeptide may comprise a single AP2 domain. The AP2 protein domain is described in detail under pfam accession number PF00847. As referred to herein, the term "dehydration-responsive element-binding proteins" or "DREB" may also encompass a C-repeat-binding protein or CBF.

Examples of DREB/CBF polypeptides include polypeptides having the following NCBI protein database accession numbers:

from *Triticum aestivum*—ABC86563; ABC86564; ABK55389; ABK55388; ABK55387; ABK55386; ABK55385; ABK55384; ABK55383; ABK55382; ABK55381; ABK55380; ABK55379; ABK55378; ABK55377; ABK55376; ABK55375; ABK55374; ABK55373; ABK55372; ABW87011; ABK55390; ABK55389; ABK55388; ABK55387; ABK55386; ABK55385; ABK55384; ABK55383; ABK55382; ABK55381; ABK55380; ABK55379; ABK55377; ABK55376; ABK55375; ABK55374; ABK55373; ABK55372; ABK55371; ABK55370; ABK55369; ABK55368; ABK55367; ABK55366; ABK55365; ABK55364; ABK55363; ABK55362; ABK55361; ABK55360; ABK55359; ABK55358; ABK55357; ABK55356; ABK55355; ABK55354; AAY32564; AAY32563; AAY32562; AAY32561; AAY32560; AAY32558; AAY32557; AAY32556; AAY32555; AAY32554; AAY32553; AAY32552; AAY32551; AAX28966; AAX28965; AAX28963; AAX28962; AAX28961; ACK99532; ACB69508; ACB69507; ACB69506; ACB69505; ACB69504; ACB69503; BAD66926; BAD66925; ABB90544; ABA08426; ABA08425; ABA08424; AAX13287; AAX13285; AAX13287; AAX13285; AAX13289; AAX13289; AAX13289; AAX13287; AAX13286; AAX13285; AAX13284; AAX13283; AAX13282; AAX13279; AAX13278; AAX13277; AAR05861; ABB84399; AAX28964; ABW87014; AAX13274 from *Triticum monococcum*—ABW87013; ABW87012; ABW87011; ABK55390; AAY32550; AAX28967;

from *Aegilops speltoides* subsp. *Speltoides*—ACO35591; ACO35590; ACO35589; ACO35588; ACO35587; ACO35586; ACO35585; ACO35584; ACO35583; AAY25517;

from *Hordeum vulgare* subsp. *Vulgare*—AAG59618; ABA25897; ABA25896; AAZ99830; AAZ99829; ACC63523; ABA25904; ABA01494; ABA01493; ABA01492; ABA01491; AAX28957; AAX28956; AAX28955; AAX28954; AAX28953; AAX28952; AAX28950; AAX28949; AAX28948; AAX23718; AAX23714; AAX23707; AAX23704; AAX23701; AAX23698; AAX23696; AAX23692; AAX23688; AAX23684; AAX23683; ABF18984; ABF18983; ABF18982; AAX28951; AAX23720; AAX23719; AAX23717; AAX23716; AAX23715; AAX23713; AAX23712; AAX23710; AAX23709; AAX23708; AAX23706; AAX23705; AAX23703; AAX23702; AAX23700; AAX23699; AAX23697; AAX23695; AAX23694; AAX23693; AAX23691; AAX23690; AAX23689; AAX23687; AAX23686; AAX23685; AAX19267; AAX19266 from *Arabidopsis thaliana*—NP_849340; NP_564496; NP_181551; NP_177844; NP_001031837; NP_567719; NP_563624; NP_196160; NP_201318; NP_191319; NP_181186; NP_181368; NP_172721; NP_176620; NP_565609; NP_172723; NP_001077764; NP_181566; NP_177681; NP_173355; NP_680184; NP_567867; NP_567721; NP_567720; NP_565929; NP_564468; NP_200015; NP_200012; NP_201520; NP_197953; NP_196720; NP_197346; NP_193098; NP_195688; NP_193408; NP_195408; NP_194543; NP_195006; NP_191608; NP_190595; NP_187713; NP_179915; NP_181113; NP_179810; NP_182021; NP_177887; NP_177631; NP_176491; NP_173695; NP_175104; NP_173609; NP_177931; NP_174636; NP_177307; NP_177301; AAP13384; AAS00621; AAO39764; AAP92125; AAL40870; AAG59619; AAN85707; NP_181186; AAX57275; Q3T5N4; Q0JQF7; Q9LWV3; Q6J1A5; Q64MA1; AAP83325; AAP83323; AAP83324; AAP83322; AAP83321; AAN02487; AAN02488; AAN02486

In some embodiments, the DREB polypeptide is a TaDREB3-like polypeptide.

A TaDREB3-like polypeptide, as referred to herein, should be understood as any DREB polypeptide which exhibits at least 60%, at least 65%, at least 70%, at least 75%, at least 80%, at least 82%, at least 84%, at least 86%, at least 88%, at least 90%, at least 92%, at least 94%, at least 96%, at least 98%, at least 99%, or 100% sequence identity to NCBI protein accession number ABC86564 and/or CRT/DRE binding factor 5 (AAY32551; Miller et al., *Mol. Genet. Genomics* 275(2), 193-203, 2006. When comparing amino acid sequences to calculate a percentage identity, the compared sequences should be compared over a comparison window of at least 50 amino acid residues, at least 100 amino acid residues, at least 150 amino acid residues, or over the full length of ABC86564 and/or AAY32551. The comparison window may comprise additions or deletions (ie. gaps) of about 20% or less as compared to the reference sequence (which does not comprise additions or deletions) for optimal alignment of the two sequences. Optimal alignment of sequences for aligning a comparison window may be conducted by computerised implementations of algorithms such as the BLAST family of programs as hereinbefore described.

In some embodiments, the TaDREB3-like polypeptide comprises a polypeptide encoded by an mRNA comprising the nucleotide sequence set forth as SEQ ID NO: 2 (NCBI accession number DQ353853).

In some embodiments the DREB polypeptide is a TaDREB2-like polypeptide.

A TaDREB2-like polypeptide, as referred to herein, should be understood as any DREB polypeptide which exhibits at least 60%, at least 65%, at least 70%, at least 75%, at least 80%, at least 82%, at least 84%, at least 86%, at least 88%, at least 90%, at least 92%, at least 94%, at least 96%, at least 98%, at least 99%, or 100% sequence identity to NCBI protein accession number ABC86563 and/or TNY (TINY) from *A. thaliana*, (NP_197953; Wilson et al., *Plant Cell* 8(4): 659-671, 1996). When comparing amino acid sequences to calculate a percentage identity, the compared sequences should be compared over a comparison window of at least 50 amino acid residues, at least 100 amino acid residues, at least 150 amino acid residues, or over the full length of ABC86563 and/or NP_197953. The comparison window may comprise additions or deletions (ie. gaps) of about 20% or less as compared to the reference sequence (which does not comprise additions or deletions) for optimal alignment of the two sequences. Optimal alignment of sequences for aligning a comparison window may be conducted by computerised implementations of algorithms such as the BLAST family of programs as hereinbefore described.

In some embodiments, the TaDREB2-like polypeptide comprises a polypeptide encoded by an mRNA comprising the nucleotide sequence set forth as SEQ ID NO: 3 (NCBI accession number DQ353852).

In some embodiments the DREB polypeptide is derived from a wheat plant as hereinbefore described.

Tolerance of transgenic plants with elevated levels of some DREB/CBF transcription factors is at least partially a result of activation of genes encoding late embryogenesis abundant (LEA) proteins known also as dehydrins (DHNs) and cold responsive (COR) genes. LEA genes are active during the maturation of embryos and desiccation of seeds in both embryo and endosperm. They are also induced by drought, cold and salt stresses in vegetative tissues. Products of these genes are often quite hydrophobic and may be involved in the direct protection of the cell from stress by increasing membrane stability and preventing incorrect folding of proteins. Cold acclimation of plants lead to LEA accumulation and increases in frost tolerance. Overexpression of particular LEA proteins in some cases lead to improvement of stress tolerance.

Thus, in some embodiments, expression of a DREB polypeptide in a plant may further upregulate the expression of one or more LEA, DHN or COR proteins.

In light of the above, in some embodiments, the present invention provides a method for improving the drought tolerance of a plant, the method comprising expressing a nucleotide sequence of interest which, when expressed by one or more cells of a plant, improves the drought tolerance of the plant, operably connected to a drought inducible transcriptional control sequence which has substantially no basal activity in the plant in the absence of drought as hereinbefore described.

As set out above, the present invention contemplates expression of a nucleotide sequence of interest under the control of a drought inducible transcriptional control sequence which has substantially no basal activity in the plant in the absence of drought.

In some embodiments, this is effected by introducing into the plant a nucleic acid which comprises a nucleotide sequence of interest operably connected to drought inducible transcriptional control sequence which has substantially no basal activity in the plant in the absence of drought.

The nucleic acid molecule may be introduced into the plant via any method known in the art. For example, an explant or cultured plant tissue may be transformed with a nucleic acid molecule, wherein the explant or cultured plant tissue is subsequently regenerated into a mature plant including the nucleic acid molecule; a nucleic acid may be directly transformed into a plant seed, either stably or transiently; a nucleic acid may be introduced into a seed via plant breeding using a parent plant that carries the nucleic acid molecule; and the like.

In some embodiments, the nucleic acid molecule is introduced into a plant cell via transformation. Plants may be transformed using any method known in the art that is appropriate for the particular plant species. Common methods include *Agrobacterium*-mediated transformation, microprojectile bombardment based transformation methods and direct DNA uptake based methods. Roa-Rodriguez et al. (*Agrobacterium*-mediated transformation of plants, 3$^{rd}$ Ed. CAMBIA Intellectual Property Resource, Canberra, Australia, 2003) review a wide array of suitable *Agrobacterium*-mediated plant transformation methods for a wide range of plant species. Other bacterial-mediated plant transformation methods may also be utilised, for example, see Broothaerts et al. (2005, supra). Microprojectile bombardment may also be used to transform plant tissue and methods for the transformation of plants, particularly cereal plants, are reviewed by Casas et al. (*Plant Breeding Rev.* 13: 235-264, 1995). Examples of direct DNA uptake transformation protocols such as protoplast transformation and electroporation are described in detail in Galbraith et al. (eds.), *Methods in Cell Biology Vol.* 50, Academic Press, San Diego, 1995). In addition to the methods mentioned above, a range of other transformation protocols may also be used. These include infiltration, electroporation of cells and tissues, electroporation of embryos, microinjection, pollen-tube pathway-, silicon carbide- and liposome mediated transformation. Methods such as these are reviewed by Rakoczy-Trojanowska (*Cell. Mol. Biol. Lett.* 7: 849-858, 2002). A range of other plant transformation methods may also be evident to those of skill in the art and, accordingly, the present invention should not be considered in any way limited to the particular plant transformation methods exemplified above.

As would be recognised by one of skill in the art, the insertion of the nucleic acid into the genome of a target cell may be either by non-site specific insertion using standard transformation vectors and protocols or by site-specific insertion, for example, as described in Terada et al. (*Nat Biotechnol* 20: 1030-1034, 2002).

In a second aspect, the present invention also provides a nucleic acid construct comprising a nucleotide sequence of interest operably connected to a drought inducible transcriptional control sequence which has substantially no basal activity in a plant in the absence of drought.

The nucleic acid construct of the second aspect of the present invention may comprise any polyribonucleotide or polydeoxyribonucleotide, which may be unmodified RNA or DNA or modified RNA or DNA. For example, the nucleic acid construct may comprise single- and/or double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the nucleic acid construct may comprise triple-stranded regions comprising RNA or DNA or both RNA and DNA. The nucleic acid construct may also comprise one or more modified bases or DNA or RNA backbones modified for stability or for other reasons. A variety of modifications can be made to DNA and RNA; thus the term "nucleic acid construct" embraces chemically, enzymatically, or metabolically modified forms.

In some embodiments, the nucleic acid construct comprises DNA. Accordingly, the nucleic acid construct may comprise, for example, a linear DNA molecule, a plasmid, a transposon, a cosmid, an artificial chromosome and the like. Furthermore, the nucleic acid construct may be a separate nucleic acid molecule or may be a part of a larger nucleic acid molecule.

In some embodiments, the drought inducible transcriptional control sequence which has substantially no basal activity in a plant in the absence of drought may be as hereinbefore described.

In some embodiments, the transcriptional control sequence is drought inducible in wheat and has substantially no basal activity in wheat in the absence of drought.

In some embodiments, the transcriptional control sequence comprises a Rab17 transcriptional control sequence as hereinbefore described.

In some embodiments, the transcriptional control sequence comprises a *Zea mays* Rab17 transcriptional control sequence or a functionally active fragment or variant thereof as hereinbefore described.

In some embodiments, the nucleotide sequence of interest comprises a nucleotide sequence which, when expressed by one or more cells of a plant, improves the drought tolerance of the plant as hereinbefore described.

In some embodiments, the nucleotide sequence of interest encodes a DREB polypeptide as hereinbefore described. In some embodiments, the DREB polypeptide is a TaDREB3-like polypeptide or a TaDREB2-like polypeptide as hereinbefore described.

In some embodiments, the nucleic acid construct may further comprise a nucleotide sequence defining a transcription terminator. The term "transcription terminator" or "terminator" refers to a DNA sequence at the end of a transcriptional unit which signals termination of transcription. Terminators are generally 3'-non-translated DNA sequences and may contain a polyadenylation signal, which facilitates the addition of polyadenylate sequences to the 3'-end of a primary transcript. As with promoter sequences, the terminator may be any terminator sequence which is operable in the cells, tissues or organs in which it is intended to be used. Examples of suitable terminator sequences which may be useful in plant cells include: the nopaline synthase (nos) terminator, the CaMV 355 terminator, the octopine synthase (ocs) terminator, potato proteinase inhibitor gene (pin) terminators, such as the pinII and pinIII terminators and the like.

The nucleic acid constructs of the present invention may further comprise other nucleotide sequences as desired. For example, the nucleic acid construct may include an origin of replication for one or more hosts; a selectable marker gene which is active in one or more hosts or the like.

As used herein, the term "selectable marker gene" includes any gene that confers a phenotype on a cell, in which it is expressed, to facilitate the identification and/or selection of cells which are transfected or transformed with a nucleic acid construct of the invention. A range of nucleotide sequences encoding suitable selectable markers are known in the art. Exemplary nucleotide sequences that encode selectable markers include: antibiotic resistance genes such as ampicillin-resistance genes, tetracycline-resistance genes, kanamycin-resistance genes, the AURI-C gene which confers resistance to the antibiotic aureobasidin A, neomycin phosphotransferase genes (eg. nptI and nptII) and hygromycin phosphotransferase genes (eg. hpt); herbicide resistance genes including glufosinate, phosphinothricin or bialaphos resistance genes such as phosphinothricin acetyl transferase-encoding genes (eg. bar), glyphosate resistance genes including 3-enoyl pyruvyl shikimate 5-phosphate synthase-encoding genes (eg. aroA), bromyxnil resistance genes including bromyxnil nitrilase-encoding genes, sulfonamide resistance genes including dihydropterate synthase-encoding genes (eg. sul) and sulfonylurea resistance genes including acetolactate synthase-encoding genes; enzyme-encoding reporter genes such as GUS and chloramphenicolacetyltransferase (CAT) encoding genes; fluorescent reporter genes such as the green fluorescent protein-encoding gene; and luminescence-based reporter genes such as the luciferase gene, amongst others.

The genetic constructs described herein may further include nucleotide sequences intended for the maintenance and/or replication of the genetic construct in prokaryotes or eukaryotes and/or the integration of the genetic construct or a part thereof into the genome of a eukaryotic or prokaryotic cell.

In some embodiments, the construct of the invention is adapted to be at least partially transferred into a plant cell via *Agrobacterium*-mediated transformation. Accordingly, in some embodiments, the nucleic acid construct comprises left and/or right T-DNA border sequences. Suitable T-DNA border sequences would be readily ascertained by one of skill in the art. However, the term "T-DNA border sequences" should be understood to include, for example, any substantially homologous and substantially directly repeated nucleotide sequences that delimit a nucleic acid molecule that is transferred from an *Agrobacterium* sp. cell into a plant cell susceptible to *Agrobacterium*-mediated transformation. By way of example, reference is made to the paper of Peralta and Ream (*Proc. Natl. Acad. Sci. USA*, 82(15): 5112-5116, 1985) and the review of Gelvin (*Microbiology and Molecular Biology Reviews*, 67(1): 16-37, 2003).

In some embodiments, the present invention also contemplates any suitable modifications to the genetic construct which facilitate bacterial mediated insertion into a plant cell via bacteria other than *Agrobacterium* sp., for example, as described in Broothaerts et al. (*Nature* 433: 629-633, 2005).

Those skilled in the art will be aware of how to produce the constructs described herein, and of the requirements for obtaining the expression thereof, when so desired, in a specific cell or cell-type under the conditions desired. In particular, it will be known to those skilled in the art that the genetic manipulations required to perform the present invention may require the propagation of a genetic construct described herein or a derivative thereof in a prokaryotic cell such as an *E. coli* cell or a plant cell or an animal cell. Exemplary methods for cloning nucleic acid molecules are described in Sambrook et al. (*Molecular Cloning: A Laboratory Manual*, Cold Spring Harbor Laboratory Press, New York, 2000).

In a third aspect, the present invention provides a genetically modified cell comprising a nucleic acid construct of the second aspect of the invention or a genomically integrated form thereof.

As referred to herein, a "genetically modified cell" includes any cell comprising a non-naturally occurring and/or introduced nucleic acid. Generally, in the case of the cells of the third aspect of the present invention, the introduced and/or non-naturally occurring nucleic acid comprises a construct of the second aspect of the invention.

Cells of the third aspect of the invention may be transformed cells which contain the construct of the second aspect of the invention, or a genomically integrated form thereof, or progeny of such transformed cells which retain the construct or a genomically integrated form thereof.

As set out above, the nucleic acid construct may be maintained in the cell as a nucleic acid molecule, as an autonomously replicating genetic element (eg. a plasmid, cosmid, artificial chromosome or the like) or it may be integrated into the genomic DNA of the cell.

As used herein, the term "genomic DNA" should be understood in its broadest context to include any and all endogenous DNA that makes up the genetic complement of a cell. As such, the genomic DNA of a cell should be understood to include chromosomes, mitochondrial DNA, plastid DNA, chloroplast DNA, endogenous plasmid DNA and the like. As such, the term "genomically integrated" contemplates chromosomal integration, mitochondrial DNA integration, plastid DNA integration, chloroplast DNA integration, endogenous plasmid integration, and the like. The "genomically integrated form" of the construct may be all or part of the construct. However, in some embodiments the genomically integrated form of the construct at least includes the nucleic acid molecule of the first aspect of the invention.

The cells contemplated by the third aspect of the invention include any prokaryotic or eukaryotic cell. In some embodiments, the cell is a plant cell. In some embodiments the cell is a monocot plant cell. In some embodiments the cell is a cereal crop plant cell.

In some embodiments, the cell is a wheat cell as hereinbefore described.

In some embodiments, the cell may also comprise a prokaryotic cell. For example, the prokaryotic cell may include an *Agrobacterium* sp. cell (or other bacterial cell), which carries the nucleic acid construct and which may, for example, be used to transform a plant. In some embodiments, the prokaryotic cell may be a cell used in the construction or cloning of the nucleic acid construct (eg. an *E. coli* cell).

In a fourth aspect, the present invention contemplates a multicellular structure comprising one or more cells of the third aspect of the invention.

In some embodiments, the multicellular structure comprises a plant or a part, organ or tissue thereof. As referred to herein, "a plant or a part, organ or tissue thereof" should be understood to specifically include a whole plant; a plant tissue; a plant organ; a plant part; a plant embryo; and cultured plant tissue such as a callus or suspension culture.

In some embodiments, the plant or a part, organ or tissue thereof comprises a monocot plant or a part, organ or tissue thereof. In some embodiments the plant or a part, organ or tissue thereof comprises a cereal crop plant or a part, organ or tissue thereof. In some embodiments, the plant or a part, organ or tissue thereof comprises a wheat plant or a part, organ or tissue thereof.

In some embodiments, a nucleotide sequence of interest is expressed in one or more cells of the plant or a part, organ or tissue thereof in response to drought.

In some embodiments, the nucleotide sequence of interest comprises a nucleotide sequence which, when expressed by one or more cells of a plant, improves the drought tolerance of the plant as hereinbefore described.

In some embodiments, the nucleotide sequence of interest encodes a DREB polypeptide as hereinbefore described. In some embodiments, the DREB polypeptide is a TaDREB3-like polypeptide or a TaDREB2-like polypeptide as hereinbefore described.

In some embodiments, the present invention also provides a plant or a part, organ or tissue thereof having improved drought tolerance, wherein the plant comprises one or more cells of the third aspect of the invention.

In some embodiments, the plant or a part, organ or tissue thereof comprises improved drought tolerance relative to a plant or a part, organ or tissue thereof which does not comprise one or more cells of the third aspect of the invention.

A plant or a part, organ or tissue thereof according to the fourth aspect of the invention may be regenerated from transformed plant material such as transformed callus, cultured embryos, explants or the like using standard techniques of the art. Such plants are typically referred to as $T_0$ plants. Plants according to the third aspect of the invention should also be understood to include progeny of $T_0$ plants. Such progeny plants may result from self fertilisation of the $T_0$ plants or crossing of the $T_0$ plants with one or more other plants of the same species, or of a different species to form hybrids. As will be appreciated, the construct of the second aspect of the invention may segregate in progeny plants, and thus the plants of the fourth aspect of the invention extend only to those progeny plants that include the construct.

Finally, reference is made to standard textbooks of molecular biology that contain methods for carrying out basic techniques encompassed by the present invention, including DNA restriction and ligation for the generation of the various genetic constructs described herein. See, for example, Sambrook and Russell, *Molecular Cloning: A Laboratory Manual* (3rd edition). Cold Spring Harbor Laboratory Press, 2001.

The present invention is further described by the following non-limiting examples:

BRIEF DESCRIPTION OF THE FIGURES

FIG. 4 shows the results of a drought tolerance experiment performed using seedlings of $T_1$ transgenic barley plants transformed with (A) 2X35S:TaDREB2 and (B) 2X35S:TaDREB3 constructs. Stress tolerance of transgenic plants is in good correlation with the expression of the transgenes. Results of northern blot hybridization are shown in the upper panels of each picture.

FIG. 5 shows the water use efficiency (WUE) of $T_2$ transgenic barley plants with constitutive expression of TaDREB2 or TaDREB3. A—Transgenic plants can grow an additional 7-10 days using the same amount of water as control plants. B—WUE of two independent lines of transgenic barley plants with up-regulated levels of TaDREB2 or TaDREB3 expression.

FIG. 13 shows transgene expression in transgenic $T_1$ barley plants transformed with pRab17:TaDREB2 and pRab17:TaDREB3 constructs before drought (line number) and under drought (line number and D) conditions. Different basal levels of transgene expression can be seen in different lines. There was no strong correlation between recovery rates and transgene expression.

FIG. 18 shows the activity of the maize Rab17 promoter in transgenic wheat plants transformed with pRab17:TaDREB2 (BW7) and pRab17:TaDREB3 (BW8) constructs shown as Q-PCR data of transgene expression. No transgene expression has been detected in plants before application of drought stress (no letter). Strong induction of the promoter can be seen after drought stress has been applied (letter S). Very low levels of promoter activity can be detected 3 weeks after re-watering (letter R) when plants were fully recovered and started flowering.

FIG. 19 shows the levels of expression of endogenous TaDREB2 (upper panel) and TaDREB3 (lower panel) in the same lines of transgenic and control plants as shown in FIG. 19.

Panel A shows the expression of transgenes under well watered (W) and drought (D) conditions; Panel B shows the up-regulation of stress responsive genes in transgenic plants expressed as fold up-regulation by drought relative to well watered and normalised against controls.

EXAMPLE 1

Gene Structure, Homologues and DNA Binding Properties

Full length cDNAs of TaDREB2 and TaDREB3 were isolated from a library prepared from wheat grain using DRE from *Arabidopsis* as bait (Lopato et al., *Plant Methods* 2: 3, 2006).

Protein sequence alignment to sequences of other DREB factors from *Arabidopsis*, rice and barley revealed that TaDREB3 belongs to the DREB1 subfamily of transcription factors and may be involved in response to cold, salt and drought stresses.

Figure 1:
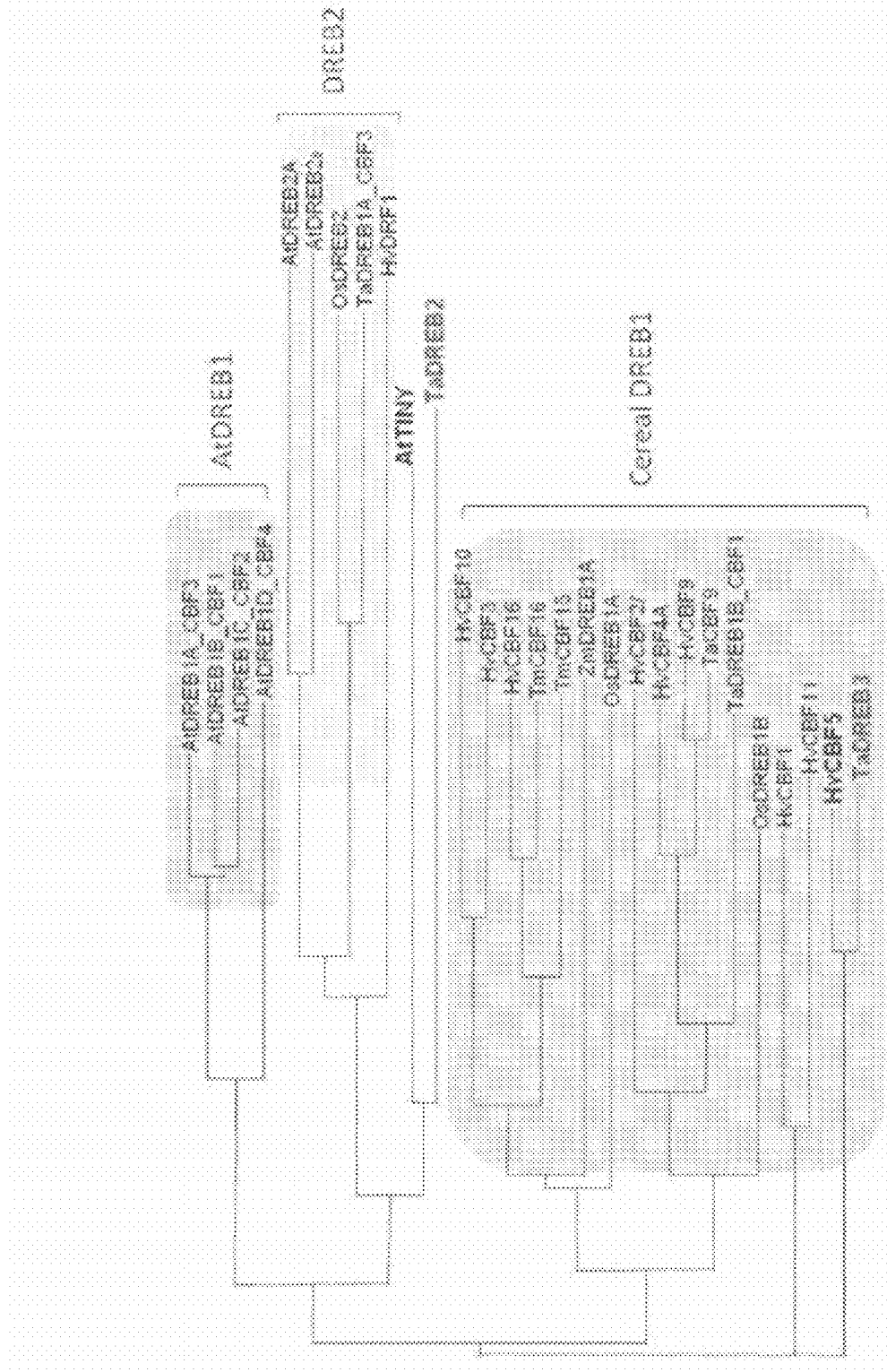
FIG. 1 shows a phylogenetic tree of the relationships of TaDREB2 and TaDREB3 to DREB factors from other plants. The tree is based on alignment of complete protein sequences.

Under drought stress, TaDREB2 activation is stronger than activation of TaDREB3. The TaDREB2 protein has higher sequence homology to TINY from *A. thaliana* and belongs to the small subfamily of proteins with sequences distinct from both DREB1 and DREB2 subfamilies (FIG. 1).

Figure 2:
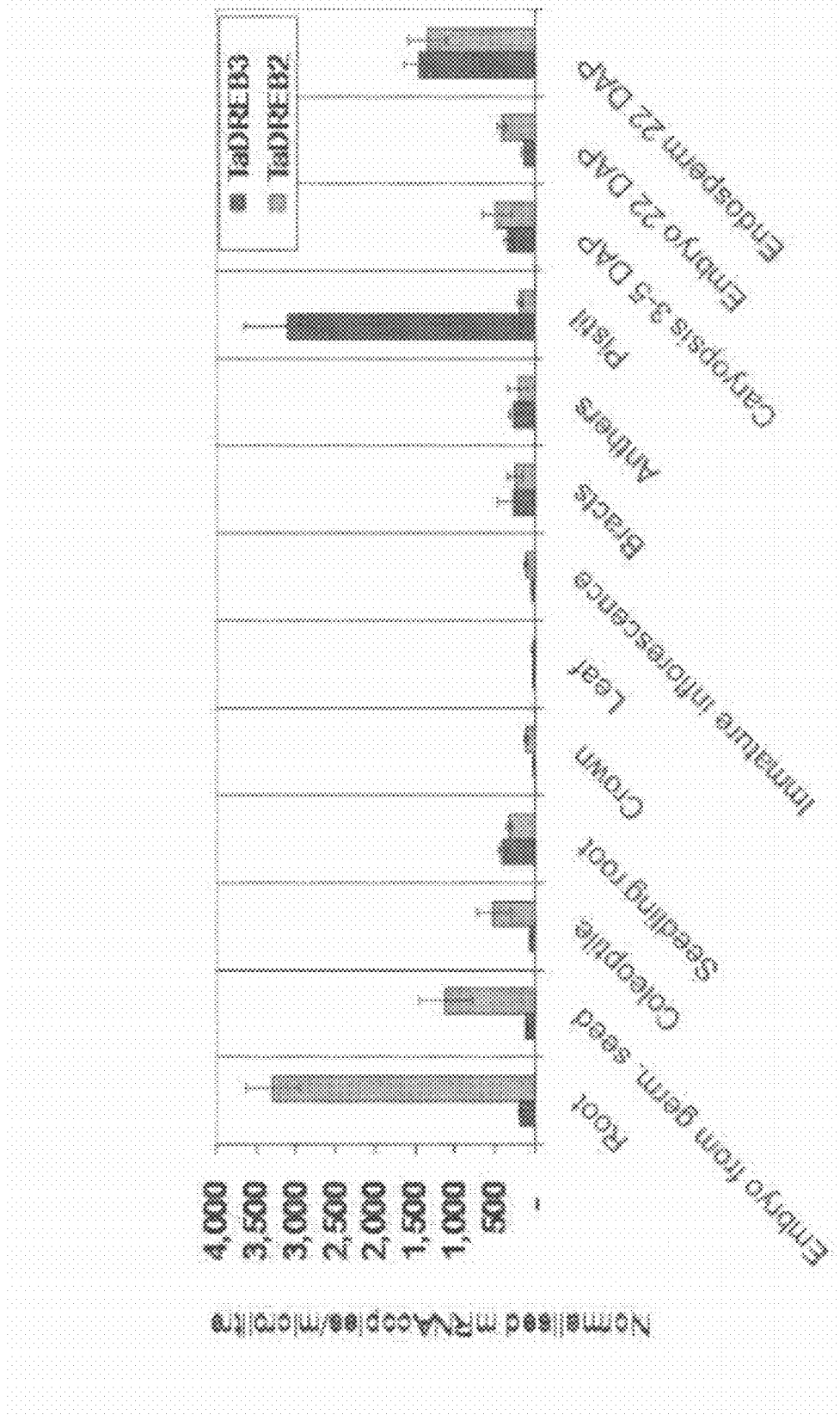
FIG. 2 shows the expression of TaDREB2 and TaDREB3 in different wheat tissues demonstrated by quantitative PCR.

Analysis of spatial expression demonstrated that both factors are expressed in the absence of stress in flower and grain tissues. A relatively high level of expression of TaDREB2 was also detected in roots (FIG. 2). In the absence of stress, substantially no expression of either transcription factor was detected in the leaf. Moreover, no induction by salt stress and very weak induction by ABA has been observed in leaf tissues.

EXAMPLE 2

Constitutive Expression of TaDREB2 or TaDREB3 Lead to Undesired Phenotypes

To examine the possibility to improve drought tolerance by up-regulation of TaDREB2 and TaDREB3, their coding regions were cloned into pMDC32 vector under the 2×35S promoter (Curtis and Grossniklaus, *Plant Physiology* 133: 462-469, 2003).

According to the inventors' previous experience the 2×35S promoter has strong activity in transgenic barley and has comparable activity to the polyubiquitin promoter from maize. However, the inventors have found 2×35S to confer only relatively weak constitutive expression in wheat.

Eleven and thirteen independent transgenic barley lines were obtained for TaDREB2 and TaDREB3, respectively, using an *Agrobacterium*-mediated transformation method (see Matthews et al., *Molecular Breeding* 7: 195-202, 2001; and Tingay et al., *Plant Journal* 11: 1369-1376, 1997).

According to the data obtained by Southern blot hybridization most transgenic $T_0$ lines had 2 to 6 copies of the transgene. In some plants all or several copies of the transgene were inserted in tandem, or very close to one another, which led to no segregation in 4 generations.

Figure 3:
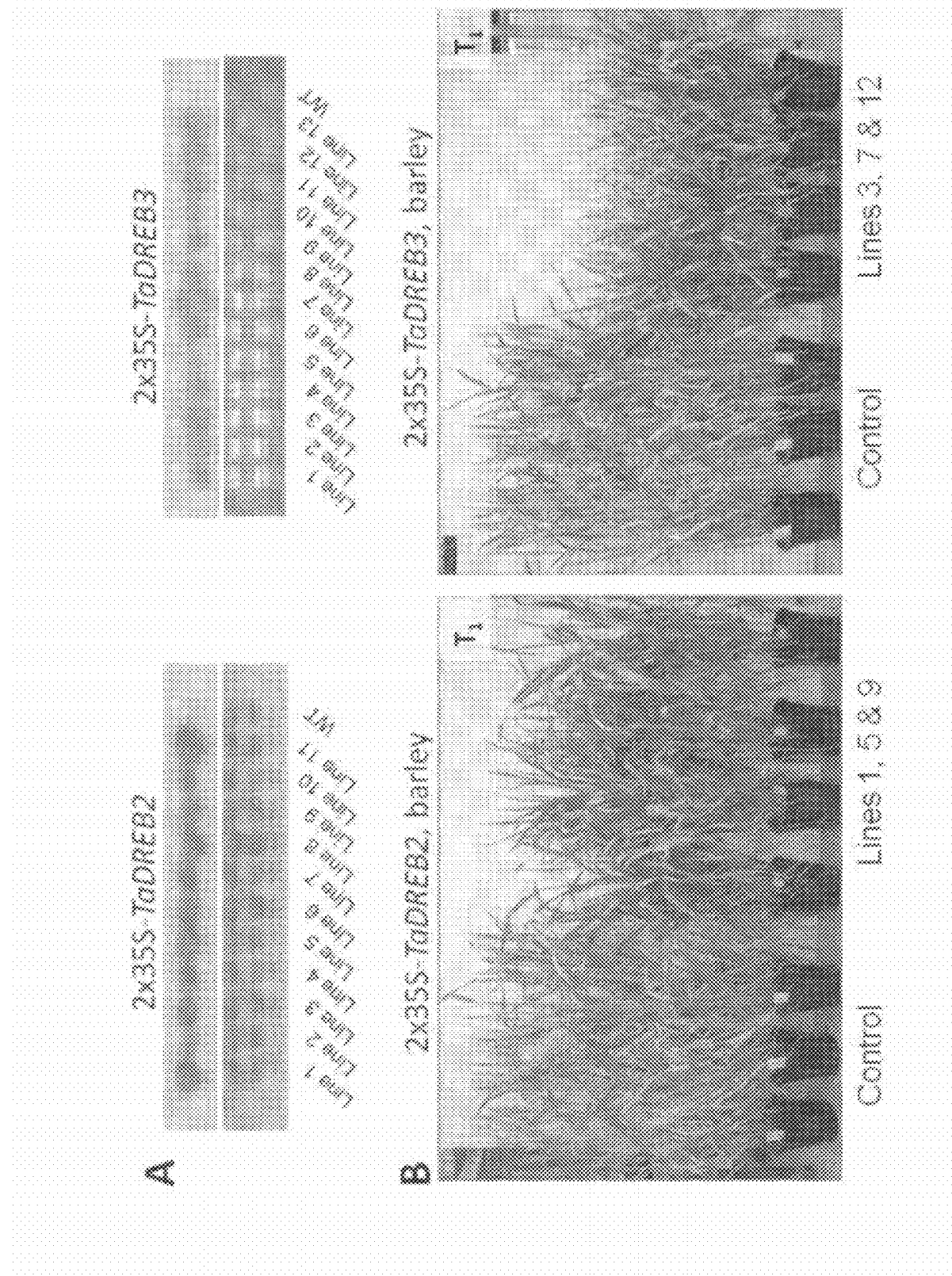
FIG. 3 shows the constitutive expression of TaDREB2 and TaDREB3 in barley plants. A—Confirmation of transgene expression in $T_0$ transgenic lines using northern blot hybridization. B—Phenotypes of $T_1$ transgenic plants at flowering stage in the absence of stress. Three independent lines are shown for each of the transgenic plants.

Expression levels of the transgenes were examined by RNA-blot analysis using total RNA from leaf tissues. Most of the $T_0$ lines had high levels of transgene overexpression (FIG. 3A). Analysis of transgenic plants was performed using four generations of plants. However, because experiments were started using $T_1$ plants, which were not homozygous and contained several copies of transgene, northern blot hybridization was used for the confirmation of transgene expression in each plant and supported plant phenotypes with levels of expression in most of the experiments. Wild type plants and plants with no transgene expression (presumably segregants) were used as a control. No difference was observed in the development and stress tolerance of the two groups of control plants.

Constitutive up-regulation of TaDREB2 and TaDREB3 caused plants to grow and develop slower than control plants and demonstrated a delay in flowering time from several weeks to one month. However, transgenic barley plants with constitutive up-regulation of TaDREB2 reached the size of control plants at flowering (FIG. 3B) and developed normal spikes. They also produced wider and darker leaves than control plants.

In contrast to TaDREB2 transgenic plants, plants with constitutive up-regulation of TaDREB3 only reached about ⅔ the size of control plants at flowering and plants with the strongest phenotype had shorter spikes (FIG. 3B). No differences in fertility or grain size were observed between both transgenics and control plants.

For transgenic plants subjected to strong drought (18 days without watering, last 14 days volumetric water content (VWC) in soil was 2-3%), after recovery the plants developed slower and started to flower later than transgenic plants that were not subjected to drought stress.

EXAMPLE 3

Drought Stress Tolerance of Barley Plants that Constitutively Express TaDREB2 or TaDREB3

To investigate whether expression of TaDREB2 and TaDREB3 increase drought tolerance of transgenic plants, four week old control (C) and either $T_1$ or $T_2$, $T_3$ and $T_4$ transgenic seedlings were subjected to 18-21 days of drought stress. Control plants started to demonstrate stress signs such as loss of turgor, leaf rolling, and loss of chlorophyll much earlier than the transgenic plants. Transgenic lines remained without changes 2-3 days longer than control plants, some of them kept turgor and showed no wilting or other signs of stress even longer (FIG. 4).

Re-watering of plants after two and half weeks of drought usually led to 95-100% loss of control plants. However most transgenic plants with confirmed gene expression survived and totally recovered within 1-2 weeks after re-watering. A good correlation between the level of transgene expression and speed of recovery was observed.

During drought tests the water content in soil, plant size, plant phenotype, time of transition to flowering after stress, and levels of transgene expression were controlled in each plant. All pots contained the same amount of soil and were watered to saturation last day before watering was stopped.

Analysis of data revealed that the difference in plant size (plant length and number of leaves) correlated with the levels of transgene expression. VWC in soil with smaller plants changed more slowly than in pots with larger plants and was about 5% on the fourth day versus 2-3% VWC in pots with control plants. It was also observed that the smallest plants demonstrated the best behavior under stress and the quickest recovery. These results indicated that the observed drought tolerance of transgenic plants in this case probably mainly reflects lower water consumption caused by slower growth and smaller size.

To confirm the above hypothesis, a similar drought test was performed with two other transgenics, which overexpress genes that have no relation to drought tolerance, but nevertheless suppress plant growth similarly to DREB factors. In this experiment, drought tolerance was observed which was similar to that observed in transgenic plants with constitutive overexpression of TaDREB2 and TaDREB3.

Although, survival of such 'placebo' transgenic plants under drought conditions was better than survival of control plants, it was not as strong as in transgenic barley with constitutively up-regulated TaDREB2 and TaDREB3, suggesting the presence of a second, real component of drought tolerance in transgenic barley with up-regulated DREB factor expression. The observed tolerance in the case of 'placebo' plants was not observed if larger pots containing several transgenic and control plants were used in the experiment. In this case, control plants had access to water remaining in the pot as a result of lower consumption of slowly growing transgenic plants.

To reveal the component related to real drought tolerance, a water use efficiency (WUE) assay was performed. This assay was based on the assumption that WUE should not be dependent on growth rate and plant size. Control and transgenic $T_2$ plants were grown in closed plastic containers with a single small hole for plant growth. Containers were filled with the same amount of soil and water and confounding water loss was significantly prevented. In three and a half weeks, soon before control plants demonstrated signs of drought stress, water use by the plants was calculated, plants were cut, dried, dry weight was measured and WUE defined.

Surprisingly, transgenic plants that constitutively overexpress TaDREB3 demonstrated about 20% higher WUE than control plants. The WUE of transgenic barley that constitutively overexpress TaDREB2 were only marginally higher than the WUE of control plants (FIG. 5).

Half of the transgenic plants used in WUE experiment were allowed to utilize the whole water supply until they died. In these plants, both transgenic plant types were able to grow for an additional 7-10 days using the same amount of water as control plants (FIG. 5).

EXAMPLE 4

Activation of Downstream Genes by Constitutive Overexpression of TaDREB2 or TaDREB3 in Barley One of the largest groups of genes up-regulated by drought, salt and cold stresses comprises late embryogenesis abundant (LEA) proteins. The expression levels of 6 different LEA genes from barley were examined in transgenic and control plants.

Figure 6:
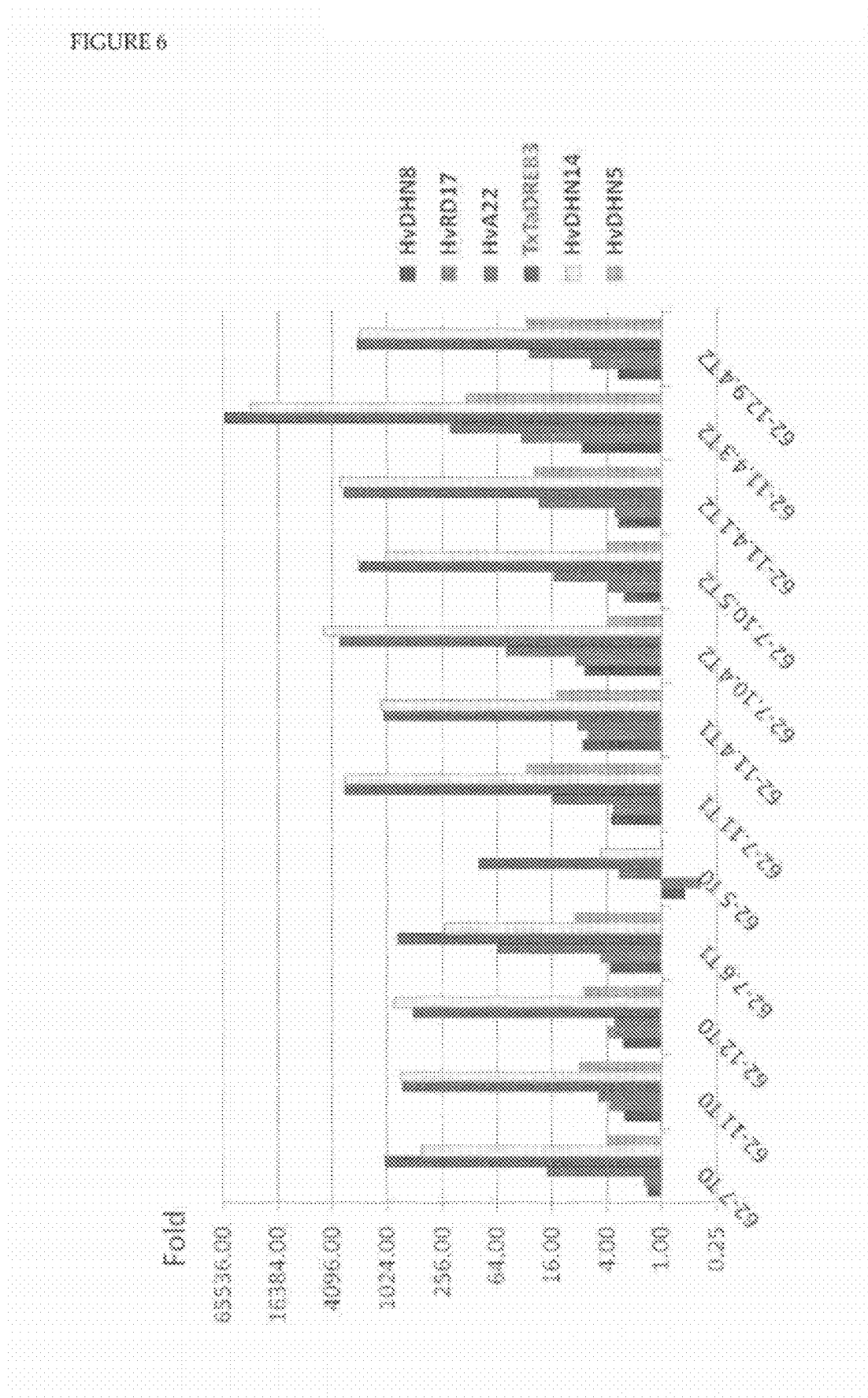
FIG. 6 shows an analysis of the expression of downstream genes in transgenic barley transformed with the 2X35S: TaDREB3 construct. The up-regulation of LEA genes in $T_0$-$T_2$ transgenic barley plants is presented as fold over expression in control plants. Expression of transgene (TxTa-DREB3) was observed to correlate with the expression of the downstream genes.

Substantial up-regulation of 5 from 6 tested LEA genes was found in plants that constitutively overexpress TaDREB3. The strongest up-regulation was shown for HvDHN14, HvDHN5 and HvA22. Expression of HvRD22, however, was not effected. A strong correlation was observed between the expression of TaDREB3 and LEA genes (FIG. 6).

Figure 7:
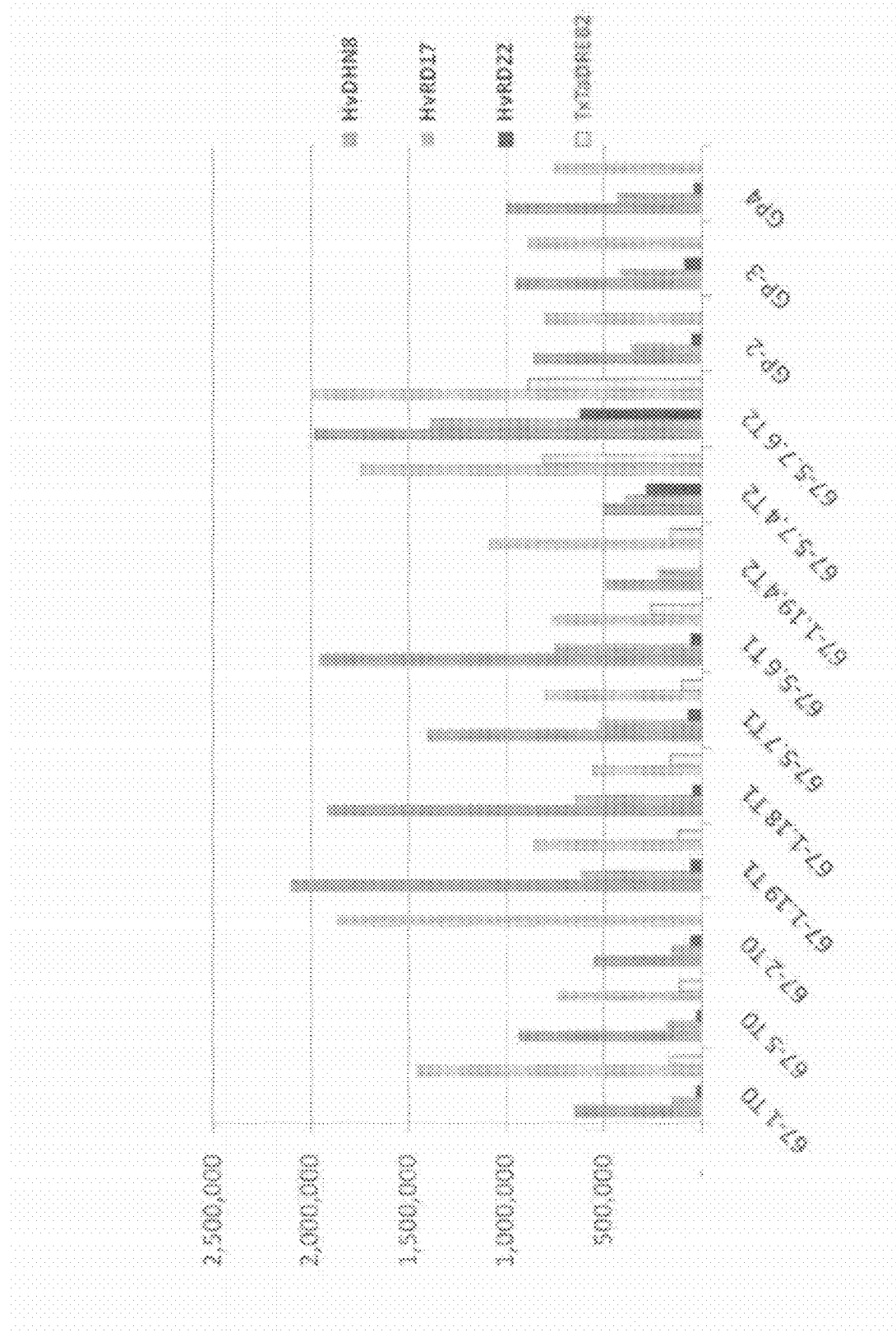
FIG. 7 shows an analysis of downstream genes in transgenic barley transformed with the 2X35S:TaDREB2 construct. Up-regulation of several LEA genes in $T_0$-$T_2$ transgenic barley plants is presented in copies per ug of RNA.

Only very mild (about two fold and less) up-regulation of two from six tested LEA genes was observed in transgenic barley that constitutively overexpress TaDREB2 (FIG. 7). The observed absence of a strong correlation between TaDREB2 transgene expression and expression of LEA genes in general may indicate indirect up-regulation of HvDHN8 and HvRD17 (FIG. 7). The ability of TaDREB3, and inability of TaDREB2, to activate the promoter of a HvDHN8-like gene from wheat in a transient assay further supports this idea (data not shown).

EXAMPLE 5

Transgenic Barley and Wheat Plants with Drought Inducible Expression of DREB Factors To eliminate undesirable phenotypes produced by constitutive expression of TaDREB2 and TaDREB3 transcription factors (and thus reduce the drought tolerance merely related growth rate and size of the plant) barley and wheat plants were transformed with constructs in which 2×35S promoter was exchanged for a 600 bp long fragment of drought and salt inducible Rab17 promoter from maize (Vilardell et al., *Plant Molecular Biology* 14: 423-432, 1990).

Transgenic wheat and barley plants were produced using biolistic bombardment and *Agrobacterium*-mediated transformation protocols, respectively. 20 independent barley lines were produced for each construct. 45 and 18 independent lines were generated for wheat transformed with pRab17:TaDREB2 and pRab17:TaDREB3, respectively.

The presence of each transgene was confirmed by PCR using primers specific for the Rab17 promoter and the nos terminator.

Drought tolerance experiments were performed using the same conditions, which were applied during tests of transgenic barley with constitutive expression of TaDREB2 and TaDREB3 (as described above), except the length of drought was 14 days (last 10 days VWC was lower than 3%).

In the case of barley, transgenic plants were still slightly smaller than control plants. However, the difference in size was observed in only some plants (generally those with the highest basal level of promoter activity) and was much less pronounced than the stunting seen in transgenic plants with constitutive overexpression of the same transcription factors.

During the 14 days after water was withheld, most transgenic barley plants behaved similarly to control plants: they lost turgor at about day 2-3 of drought, rolled leaves, and became chlorotic. However, several smaller plants looked generally more healthy than control plants one week after the end of watering.

Figure 8:
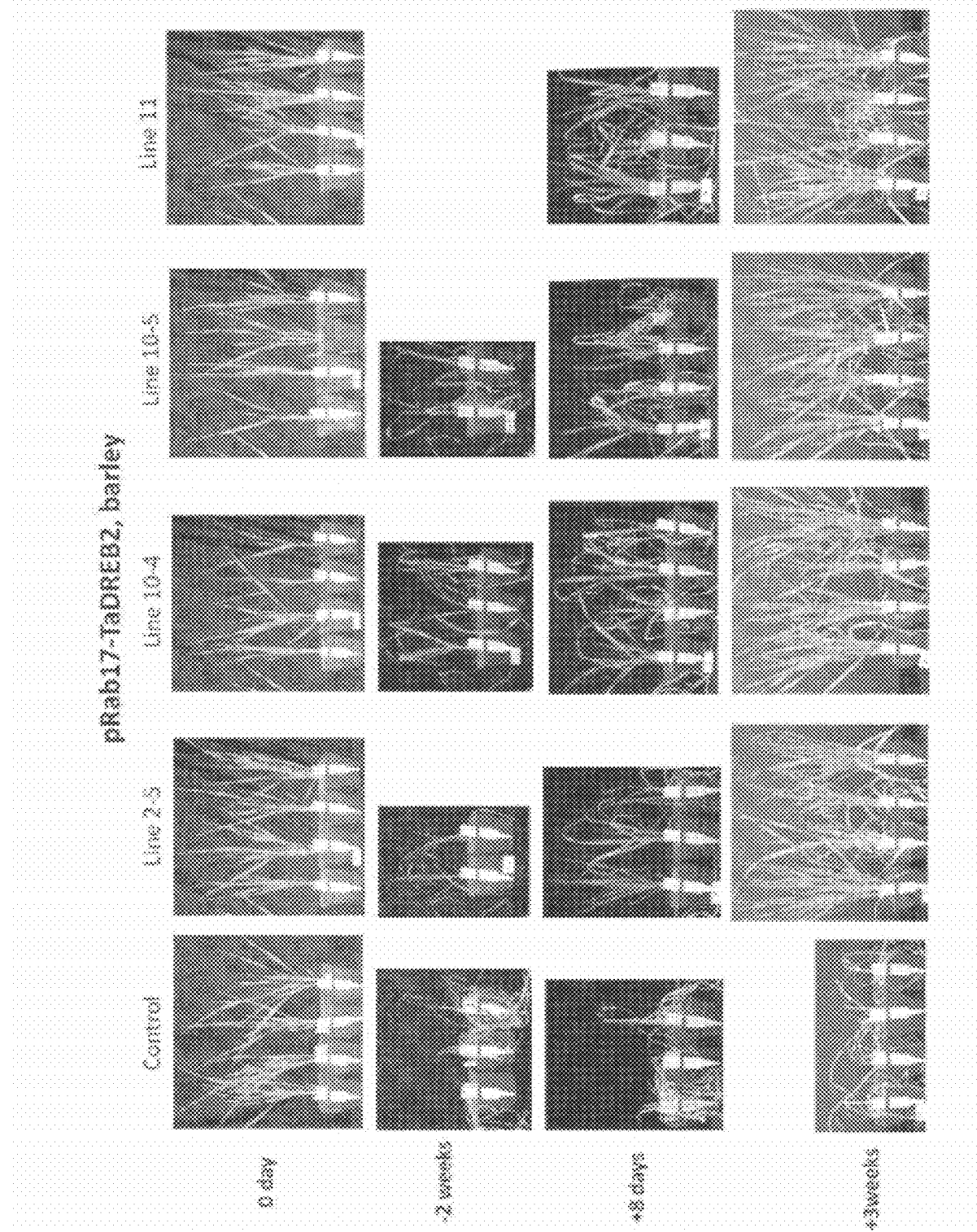
FIG. 8 shows the results of a drought tolerance experiment using $T_1$ transgenic barley plants with drought inducible expression of TaDREB2. 0 day—day before water was withheld; −2 weeks—2 weeks without watering; +8 days—8 days after re-watering; +3 weeks—3 weeks after re-watering.
Figure 9:
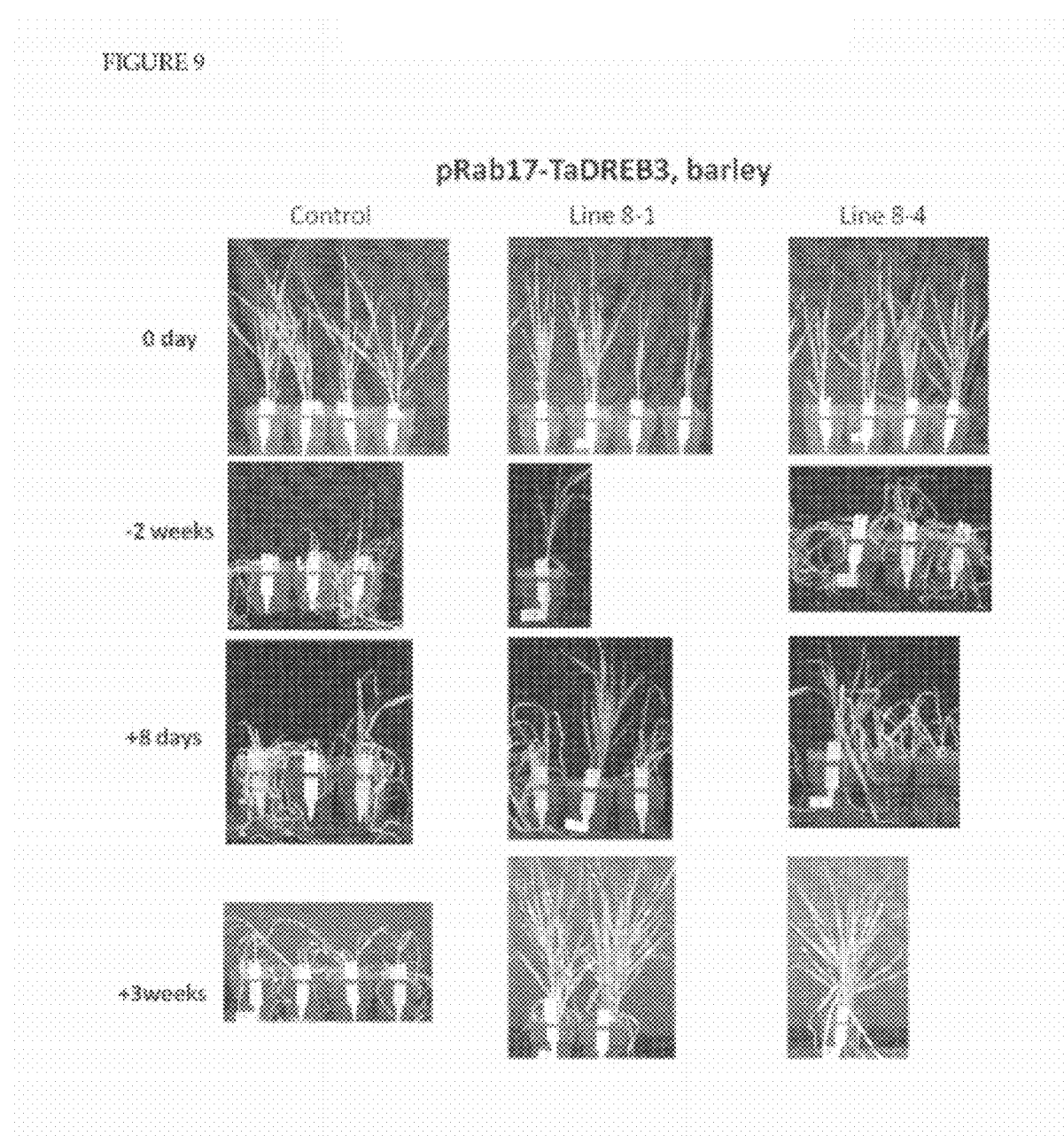
FIG. 9 shows the results of a drought tolerance experiment using $T_1$ transgenic barley plants with drought inducible expression of TaDREB3. 0 day—day before water was withheld; −2 weeks—2 weeks without watering; +8 days—8 days after re-watering; +3 weeks—3 weeks after re-watering.

In contrast to control plants, which all died, most transgenic plants with confirmed transgene overexpression quickly recovered after re-watering (FIGS. 8 and 9). Transgenic plants appeared to recover within one week after re-watering and started to flower after 4-5 weeks. No changes in spike size or number were observed. However, transgenic barley plants which were subjected to drought stress initiated flowering before at a smaller size than plants which were not subjected to drought.

In contrast to transgenic barley plants, transgenic wheat lines transformed with pRab17-TaDREB2 and pRab17-TaDREB3 constructs showed no developmental delay or retardation. At the beginning of the drought conditions, the transgenic wheat plants looked generally indistinguishable from the control plants.

Figure 20:
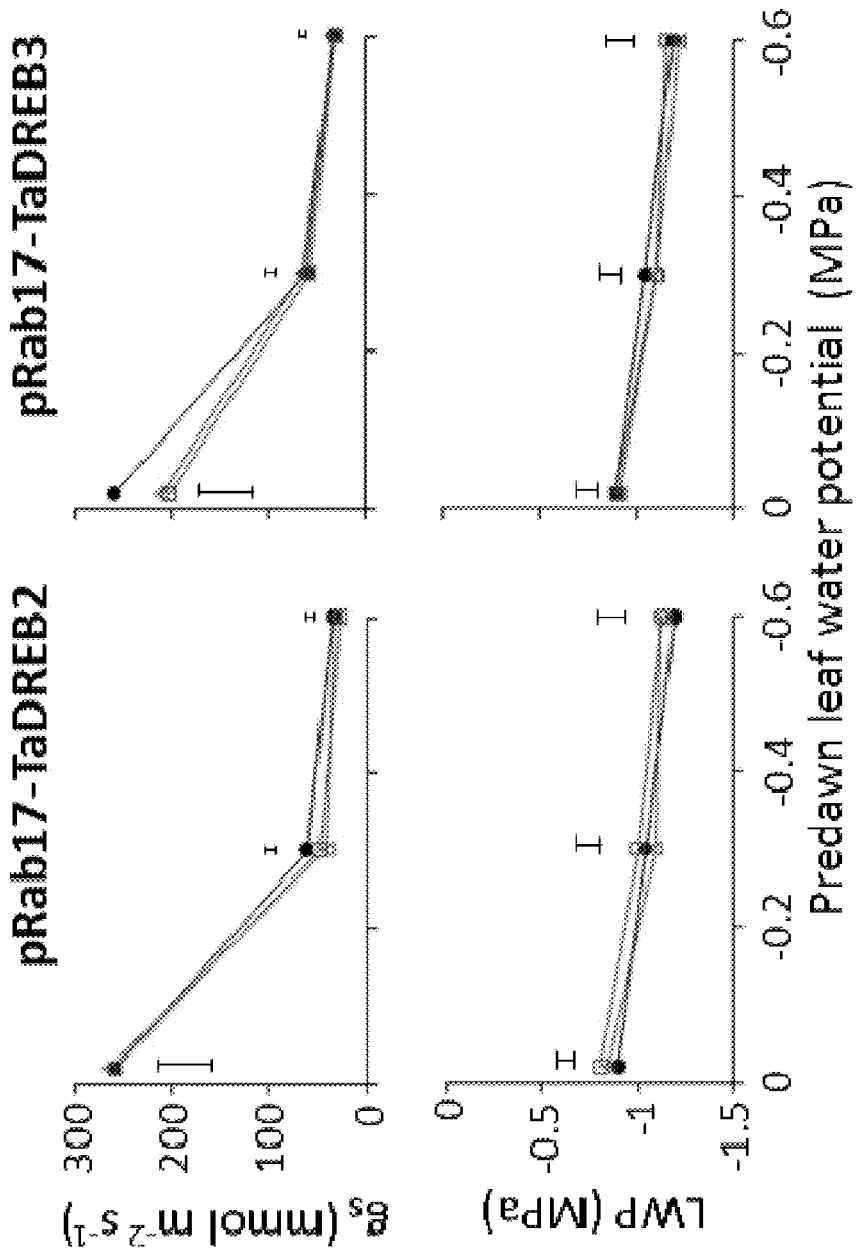
FIG. 20 shows the behaviour of wheat plants with drought inducible expression of TaDREB2 and TaDREB3 during a "survival" drought tolerance test under moderate water deficit. The graphs show stomatal conductance and leaf water potential of mature leaves at midday for two TaDREB2 transformed lines (L2-4-3, triangle, and L5-4, square; left panels), two TaDREB3 transformed lines (L7-7-1, triangle and L10-2-2, square; right panels) and control plants (black dots and lines) measured for three water regimes (well watered, −0.3 and −0.6 MPa of predawn leaf water potential). I=error bar.

For example, under well watered conditions and under moderate water deficit (until 5% of VWC, −0.6 MPa), the stomatal conductance of the transformed plants were similar to that of control plants, decreasing from 238±29 to 32±3 mmol m$^{-2}$ s$^{-1}$ with soil drying. This resulted in no difference in leaf water status, regardless to the soil water status, with leaf water potential decreasing only slightly with soil drying, from −0.87 MPa under well watered conditions to −1.16 MPa under drought (see FIG. 20).

During the period of drought, the behavior of the control and transgenic plants was also generally similar: all plants were drying with the same speed and looked substantially dry and dead at the last day before re-watering.

Figure 21:
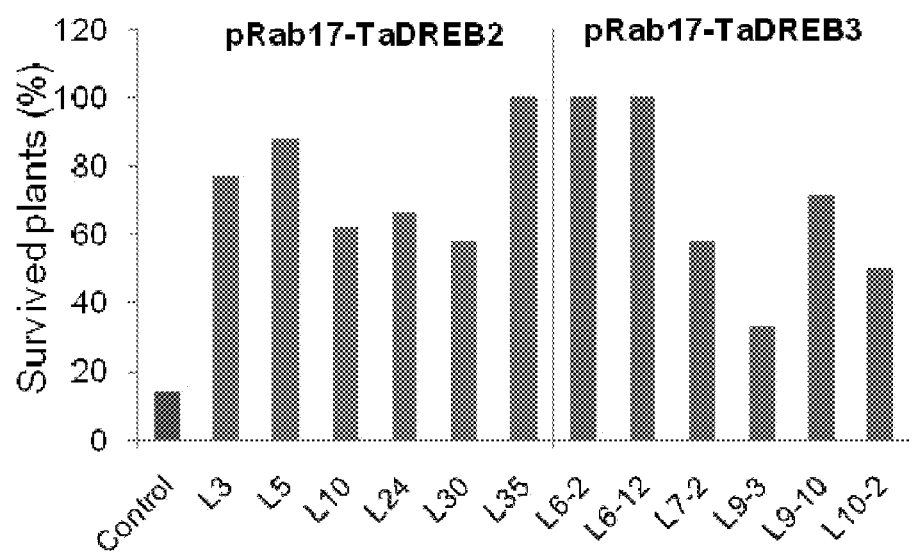
FIG. 21 shows the behaviour of wheat plants with drought inducible expression of TaDREB2 and TaDREB3 during a "survival" drought tolerance test. The graphs show the percentage of plants that survived for several independent plant lines transformed with either pRab17-TaDREB2 and pRab17-TaDREB3 compared to control plants.

However, one week after re-watering ~90% of control plants still appeared dead, whereas a much higher percentage of transgenic plants started to recover (see figure 21).

Figure 10:
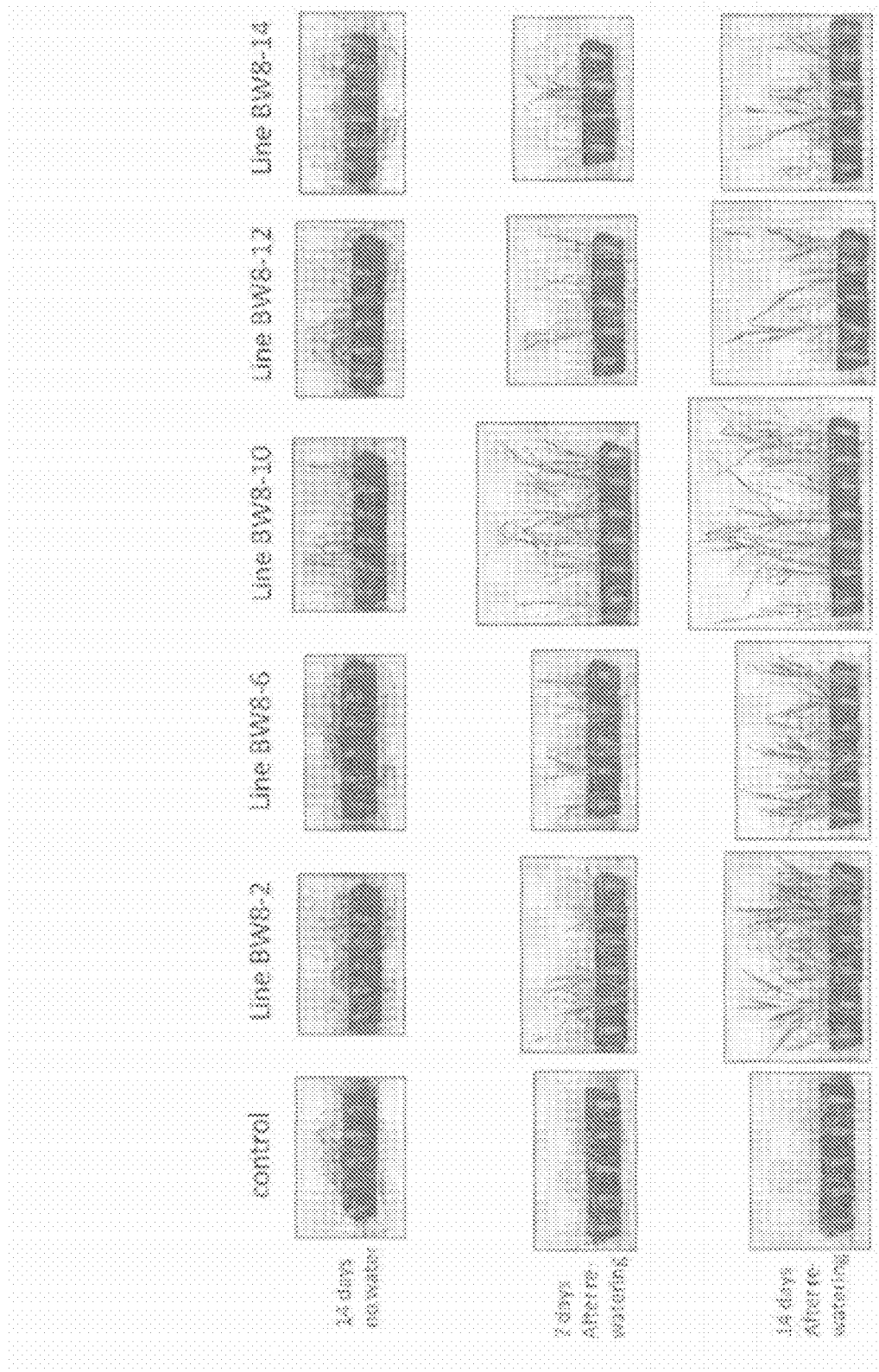
FIG. 10 shows the results of a drought tolerance experiment using $T_1$ transgenic wheat plants with drought inducible expression of TaDREB3. Plants are shown after 18 days of drought, and 7 and 14 days after re-watering.
Figure 11:
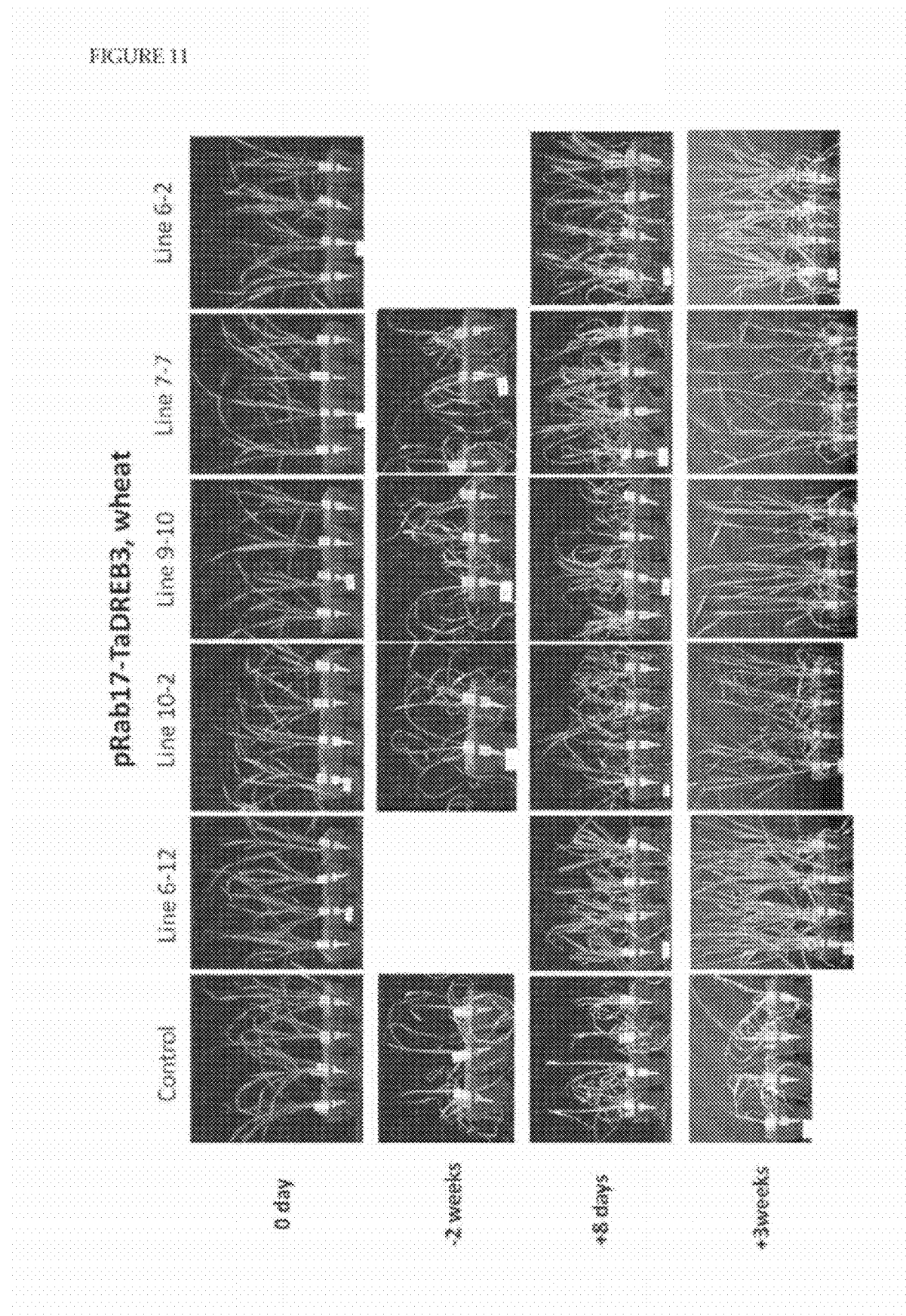
FIG. 11 shows the results of drought tolerance experiment using $T_2$ transgenic wheat plants with drought inducible expression of TaDREB3. 0 day—day before water was withheld; −2 weeks—2 weeks without watering; +8 days—8 days after re-watering; +3 weeks—3 weeks after re-watering.
Figure 12:
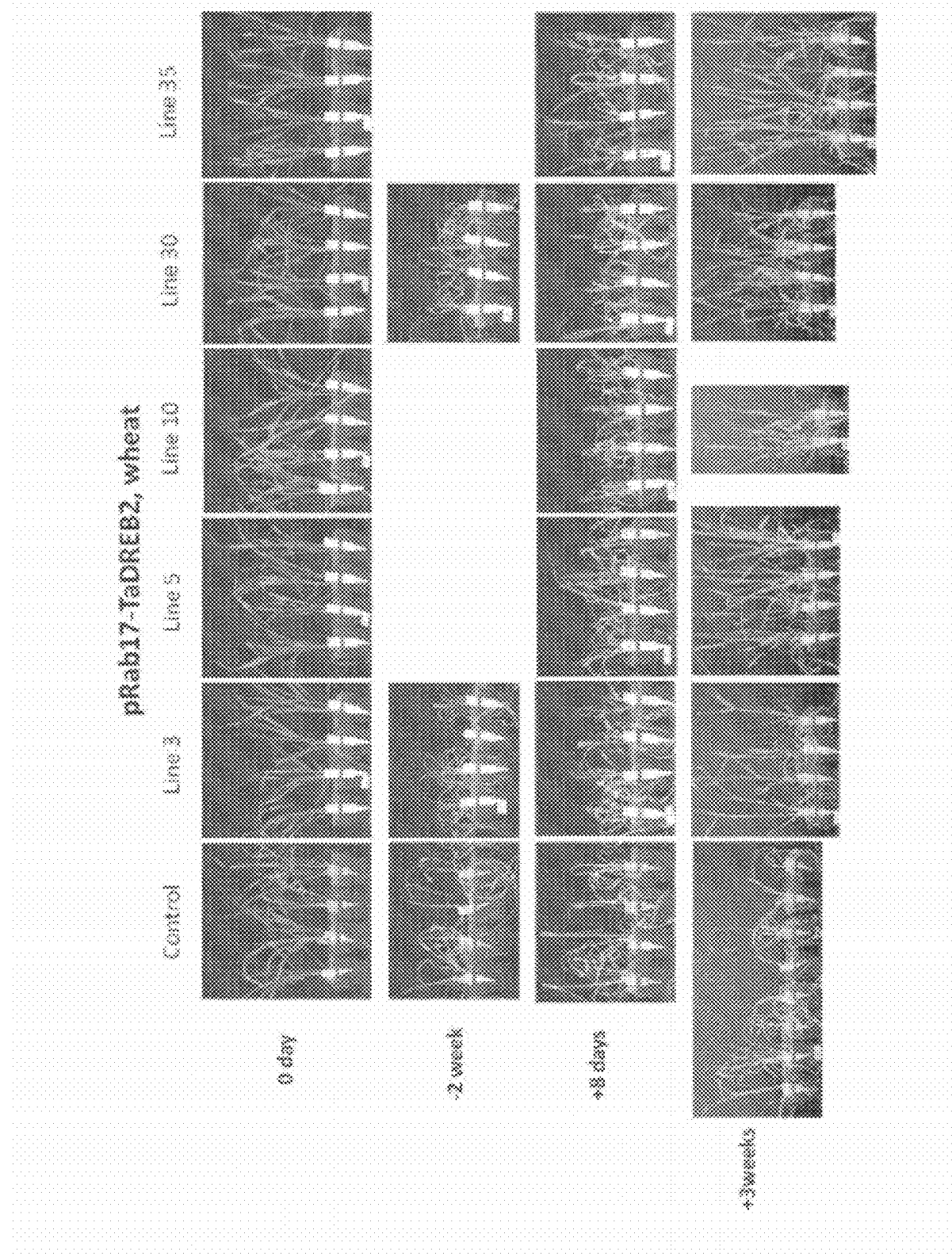
FIG. 12 shows the results of a drought tolerance experiment using $T_1$ transgenic wheat plants with drought inducible expression of TaDREB2. 0 day—day before water was withheld; −2 weeks—2 weeks without watering; +8 days—8 days after re-watering; +3 weeks—3 weeks after re-watering.

Plants transformed with pRab17:TaDREB3 recovered generally much faster than plants transformed with pRab17:TaDREB2, and started to flower about three weeks after re-watering (FIGS. 10 and 11). Wheat plants transformed with pRab17:TaDREB2 started to flower 3-4 days later (FIG. 12).

Several weeks after recovery both transgenic plant types looked generally normal, developed many spikes of normal size and the number of sterile flowers and aborted grain did not exceed the equivalent numbers in control plants.

Two of the twenty control plants survived the drought stress, but recovered much slower than transgenic plants. They remained very small (⅓ of normal size) when flowering and only produced 2 and 1 small spikes, respectively.

EXAMPLE 6

Activity of Maize Rab17 Promoter in Wheat and Barley

Northern blot analysis of expression of DREB factors under the Rab17 promoter were performed using leaf samples, which were collected one day before watering was stopped, 3 days after watering was stopped, and 3 weeks after re-watering was started.

A relatively high basal level of activity of the Rab17 promoter in the absence of stress was observed in barley plants (FIG. 13). Levels of basal activity were different in different independent lines. Developmental phenotypes observed in some plants correlated with higher levels of basal promoter activity.

Figure 14:
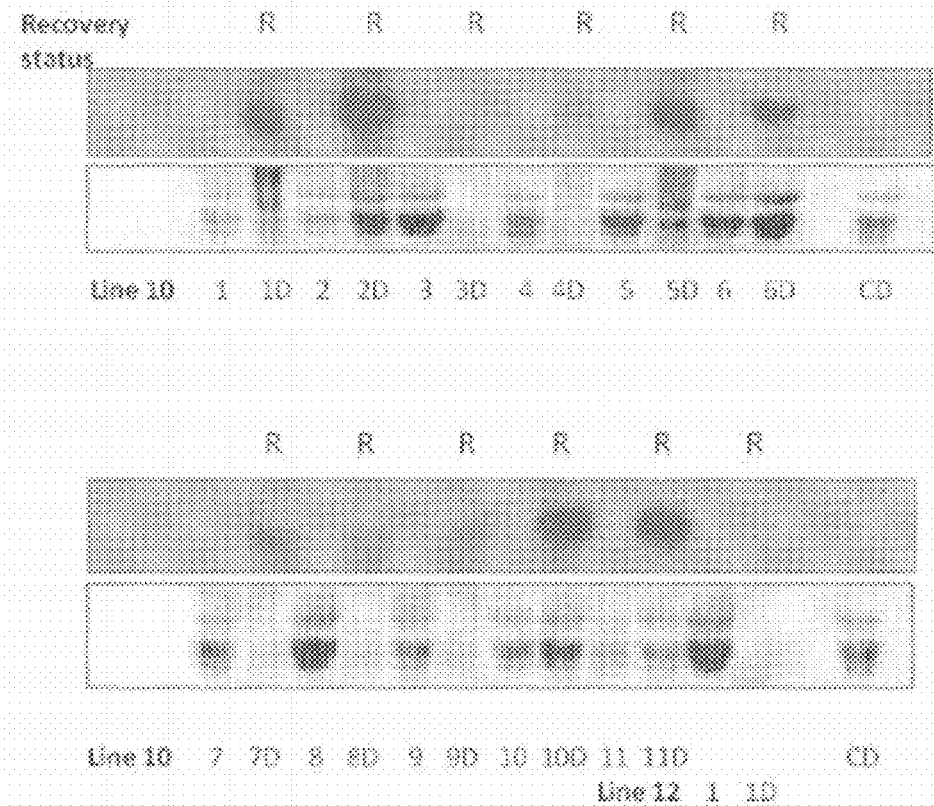
FIG. 14 shows transgene expression in transgenic $T_1$ wheat plants transformed with pRab17:TaDREB3 constructs under control (line number) and drought (line number and D) conditions. No basal level of promoter activity and differences in plants were observed before stress. There was good correlation between recovery and transgene expression.
Figure 15:
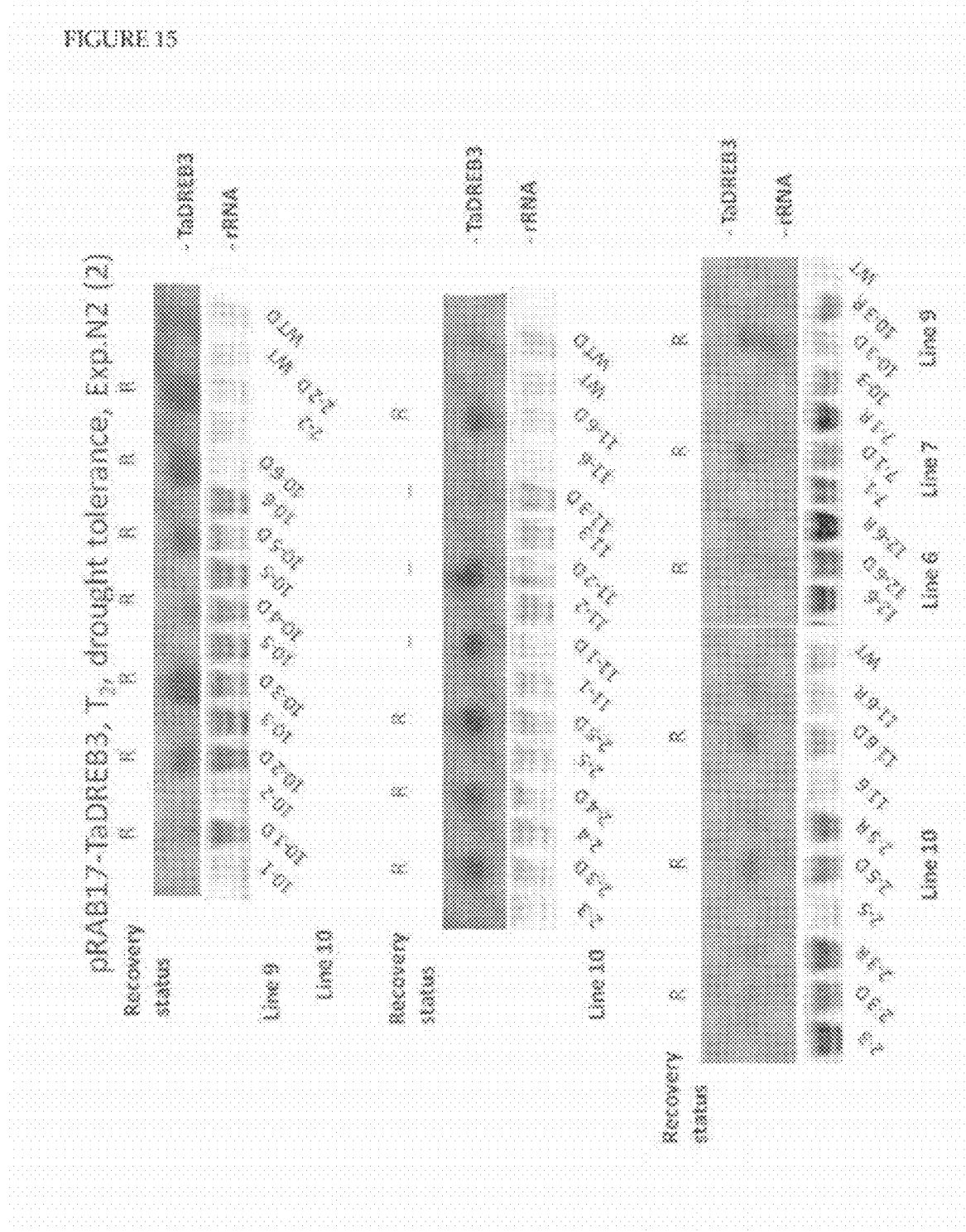
FIG. 15 shows transgene expression in transgenic $T_2$ wheat plants transformed with pRab17:TaDREB3 constructs under control (line number) and drought (line number and D) conditions. No basal level of promoter activity and differences in plants were observed before stress.
Figure 16:
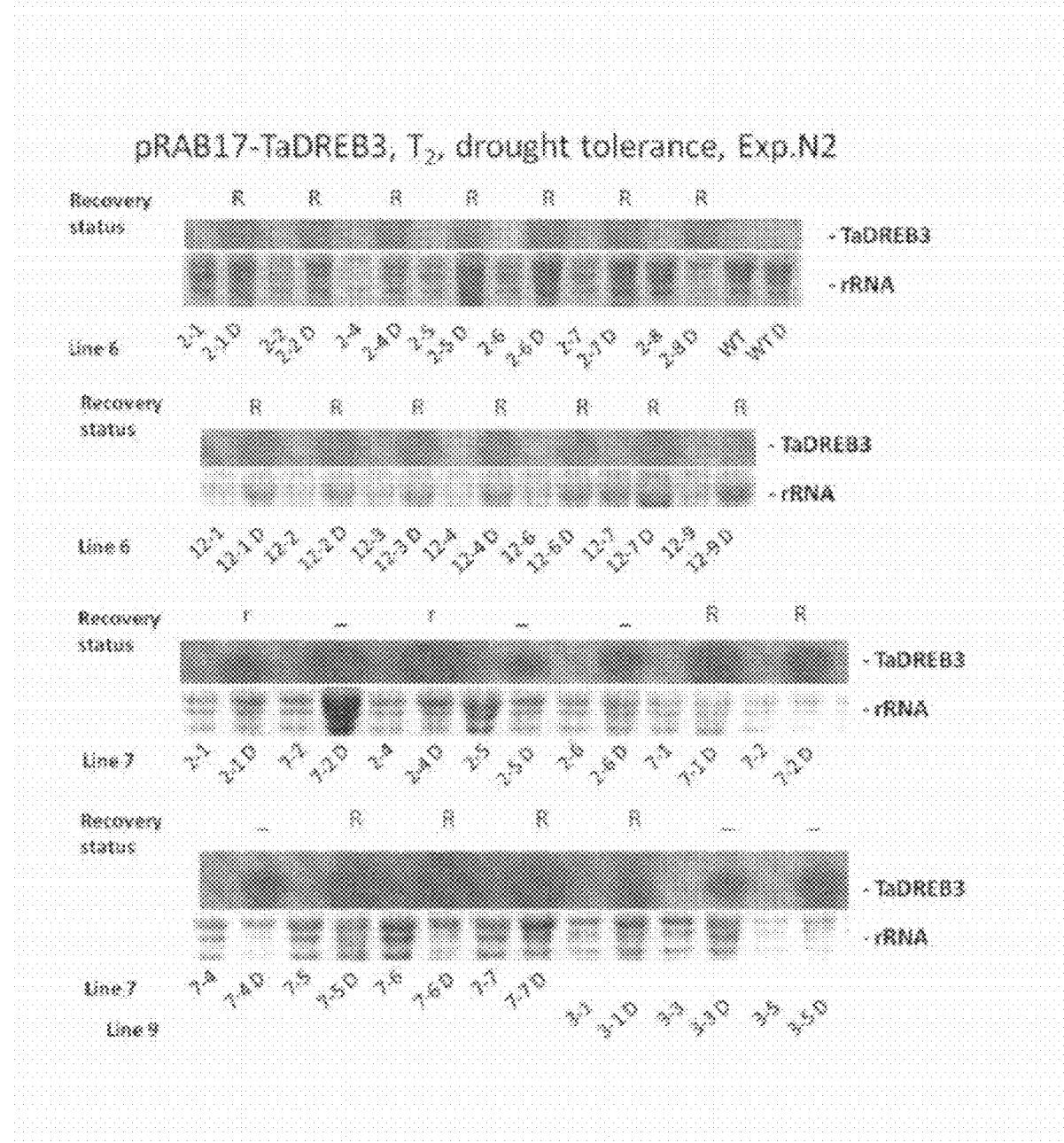
FIG. 16 shows transgene expression in transgenic $T_2$ wheat plants transformed with pRab17:TaDREB3 constructs before drought (line number), under drought (line number and D), and 3 weeks after recovery (line number and R). No basal level of promoter activity and differences in plants were observed before and after stress.

Surprisingly, no basal activity of the maize Rab17 promoter was detected by northern blot hybridization in wheat. However, under drought stress the promoter was quickly and strongly activated (FIG. 14-16). This limited activity of DREB expression to within a period of stress and several days of recovery and thus led to the absence of any undesired changes in plant development before and after stress.

In both barley and wheat re-watering caused deactivation of the promoter. However, low levels of transgene transcripts were detected up to three weeks after re-watering (FIG. 16). The presence of this low level of transgene mRNA can be explained by the high stability of the subject mRNAs (eg. the nos terminator of pMDC32 vector provides a very stable mRNA) rather than by any remaining activity of the promoter. No negative influence of the remaining transgene transcripts was observed on transition time to flowering, size, number and shape of spikes and size of grain.

Figure 17:
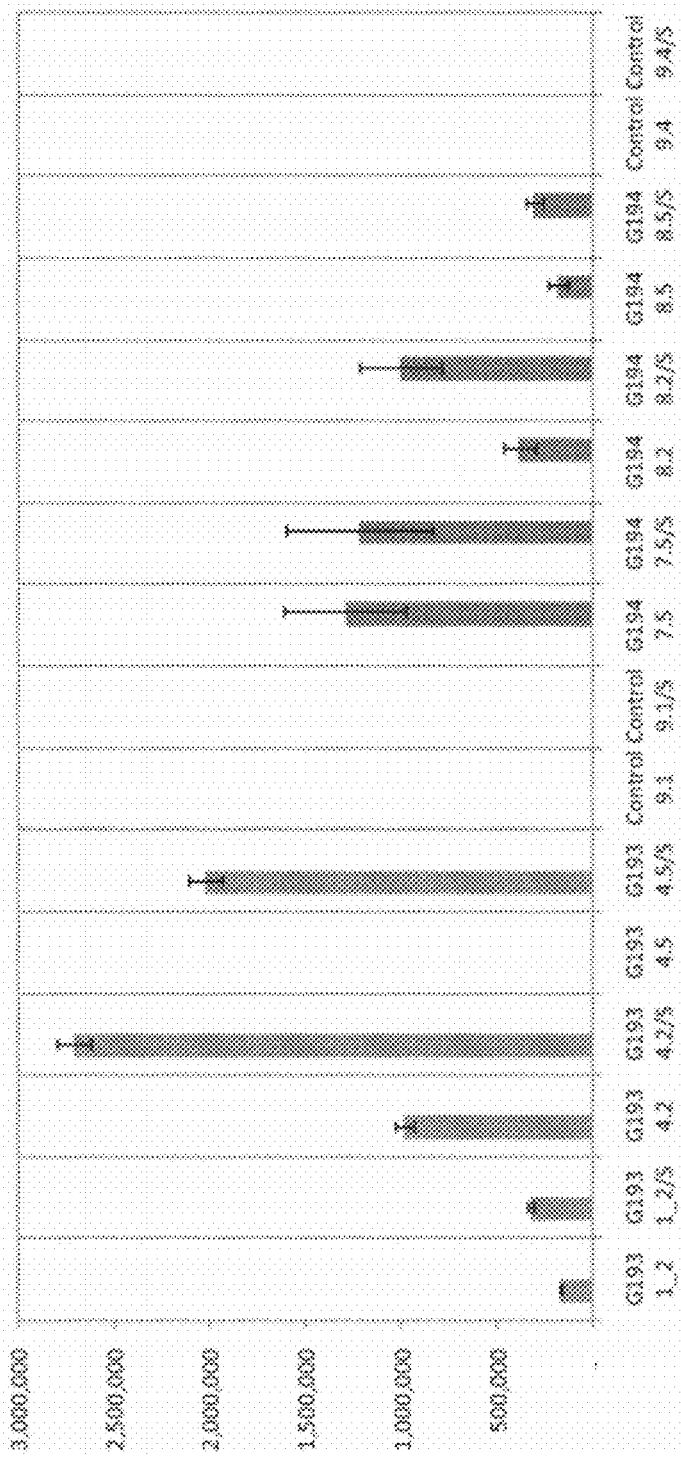
FIG. 17 shows the activity of the maize Rab17 promoter in transgenic barley plants transformed with pRab17:TaDREB2 (G193) or pRab17:TaDREB3 (G194) constructs shown as Q-PCR data of transgene expression. High levels of transgene expression can be seen in plants before application of drought stress (no letter). Some induction of the promoter can be seen after drought stress has been applied (letter S) (1-2% VWC in soil, plants demonstrated clear signs of stress).

FIGS. 17 to 19 show the activity of the maize Rab17 promoter in wheat and barley as measured using Q-PCR. As shown in FIG. 17, in barley, transgene expression can be seen in plants before application of drought stress, although some induction of the promoter can be seen after drought stress has been applied.

In contrast, FIG. 18 shows the activity of the maize Rab17 promoter in transgenic wheat plants where no transgene expression was detected in plants before application of drought stress. In addition, strong induction of the promoter can be seen after drought stress has been applied.

FIG. 19 shows the levels of expression of endogenous TaDREB2 and TaDREB3 in the same lines of transgenic and control plants as shown in FIG. 18. As can be seen from the Y-axis scale, the level of endogenous TaDREB2 and TaDREB3 is substantially lower than the level of expression directed by the Rab17 promoter.

EXAMPLE 7

Activation of Stress Inducible Genes by Inducible Over-expression of DREB Factors in Wheat Expression of nine wheat LEA/COR/DHN genes known to be induced by drought and cold were examined in the transgenic plants. The expression results were initially used to determine a ratio of expression levels under drought stress (time of sampling: 4 days after soil VWC reached 2%) relative to well-watered conditions. These data are then used to calculate the increase in induction of expression in transgenic plants relative to induction in control plants (see FIG. 22). This reflects additional induction of these genes by DREB transgenes relative to induction solely by drought and potentially related to the effects of the endogenous DREB genes.

Figure 22:
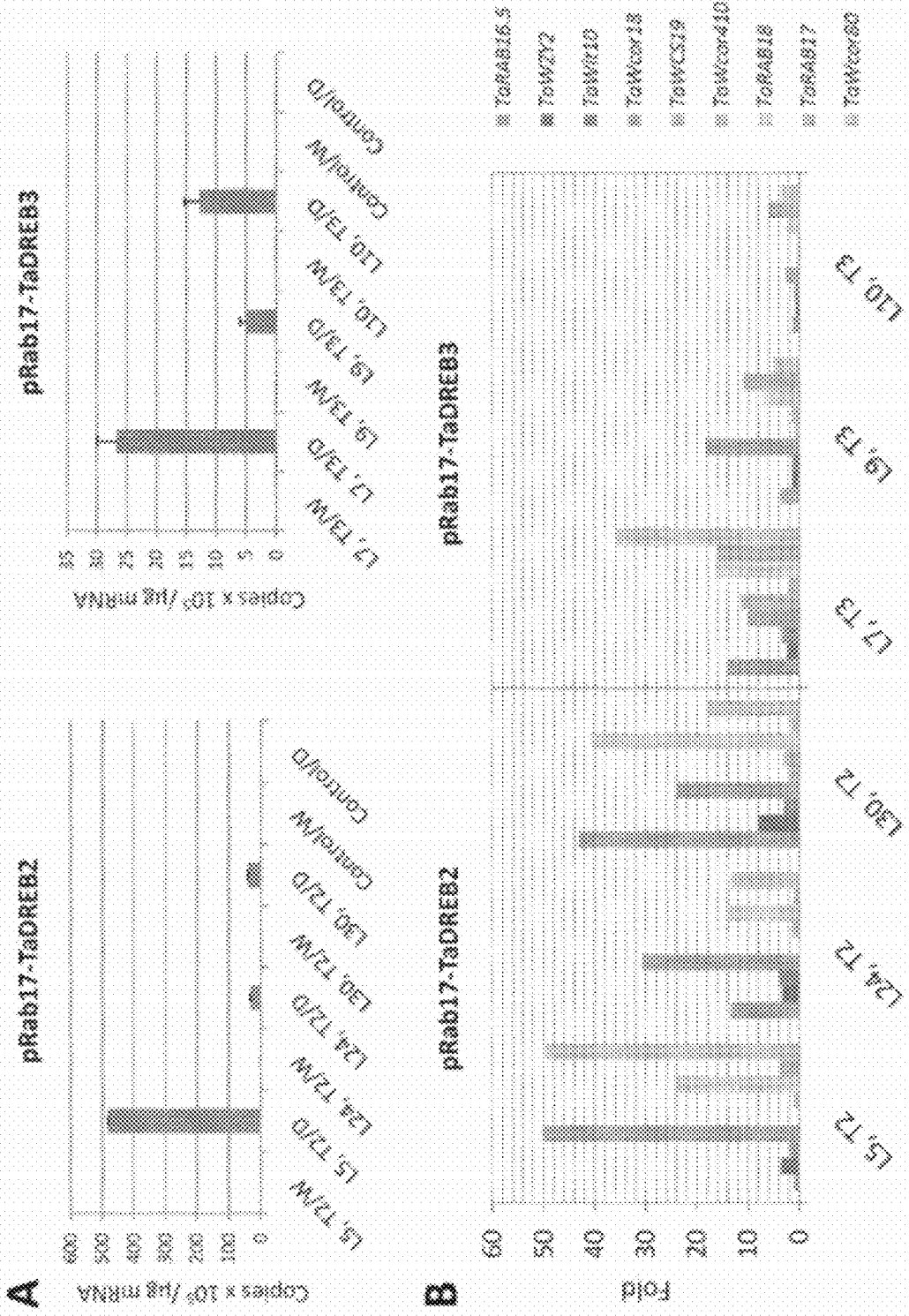
FIG. 22 shows the expression of the transgene and stress inducible LEA/COR/DHN genes in transgenic wheat plants with inducible over-expression of TaDREB2 and TaDREB3.

As shown in FIG. 22, induction by the transgene reached 50 fold for some LEA/COR/DHN genes, although most genes showed lower induction. Activation of some LEA/COR/DHN genes also appeared to be specific for only one of the transgenes. For example, the induction of expression of TaRAB17 was much stronger in TaDREB3 transgenic lines while induction of expression of TaWZY2 was stronger in TaDREB2 transgenic plants.

EXAMPLE 8

Materials and Methods

Plasmid Construction and Transformation of Wheat and Barley

The full length coding regions of TaDREB2 and TaDREB3 were amplified by PCR using AccuPrime™ Pfx DNA polymerase (Invitrogen). Full length cDNAs of TaDREB2 (Acc. DQ353852; SEQ ID NO: 3) and TaDREB3 (Acc. DQ353853; SEQ ID NO: 2) isolated in the Y1H screen from wheat grain cDNA library (Lopato et al., *Plant Methods* 2: 3, 2006) were used as templates. Coding regions of TaDREB2 and TaDREB3 cDNAs were cloned into: (i) the pMDC32 vector (Curtis and Grossniklaus, *Plant Physiology* 133: 462-469, 2003) downstream of the vector's duplicated 35S promoter; and (ii) a pMDC32 vector in which the 2X35S promoter was excised using HindIII-KpnII restriction sites and replaced with a 634bp fragment of the ZmRab17 promoter (Busk et al., *Plant Journal* 11: 1285-1295, 1997).

All four constructs were transformed into barley (*Hordeum vulgare* L. cv. Golden Promise) using *Agrobacterium*-mediated transformation using the method developed by (Tingay et al., *Plant Journal* 11: 1369-1376, 1997) and modified by (Matthews et al., *Molecular Breeding* 7: 195-202, 2001).

Wheat (*Triticum aestivum* L. cv. Bobwhite) was transformed using Holistic bombardment. pRab17:TaDREB2:nos and pRab17:TaDREB3:nos were excised from the respective constructs using PmeI and BsaXI, gel purified and co-transformed together with the Ubi:hpt:nos cassette (3676 bps fragment of the vector plasmid, cut with PmeI-SmaI) into wheat using microprojectile bombardment. Transgene presence and expression in $T_0$ transgenic plants and/or $T_1$ generation plants were analysed by Southern and northern blot hybridization as described by Sambrook and Russell (*Molecular Cloning: A Laboratory Manual*, 3rd edition, Cold Spring Harbor Laboratory Press, 2001)

Plant Growth and Stress Conditions

For phenotype analysis plants were grown in glasshouse conditions with an average day/night temperature of 25° C./16° C. and 15 h day length. $T_1$ and $T_2$ generation plants were monitored for phenotype changes, such as growth rate, plant height, heading time, number of tillers, spike phenotype, grain phenotype and yield.

Seedlings for drought tolerance testing were grown in growth rooms, with a 16 h day length at day/night temperatures of 24° C./16° C. $T_1$-$T_4$ generation plants were grown in 4 inch pots for four weeks and the volumetric water content (VWC) of the pots was monitored. At 4 weeks water was withheld. In about 4 days pots reached 1-2% VWC and clear wilting of control plants was observed. The plants were kept 10 to 17 more days without watering and then re-watered.

Plants were assessed for recovery after one and three weeks of re-watering and stress tolerant plants were transferred to the glasshouse for observation of development and generation of seeds. Water use efficiency (WUE) of transgenic plants was determined using a seedling assay where seeds of similar size were sown in 450 ml pots (15 cm height×7 cm diameter). Each pot contained 400 g of soil and the same amount of water. The pots were covered with a plastic sheet to prevent evaporation of water. The plants were grown until there was no extractable water left. Total plant water use was calculated by subtracting the final pot weight from starting weight, factoring in water loss through evaporation. WUE was then calculated in grams of dry shoot biomass per ml of water used.

Northern Blot and Q-PCR Analysis

All plants which were used in our experiments were controlled for transgene expression using northern blot hybridization, which was performed as described elsewhere (Sambrook and Russell, *Molecular Cloning: A Laboratory Manual*, 3rd edition, Cold Spring Harbor Laboratory Press, 2001). Q-PCR analysis was used to characterize expression of TaDREB2 and TaDREB3 in different wheat tissues and to analyse expression of downstream genes. It was performed using primers derived from 3' untranslated regions of respective cDNAs. The procedure and normalization was described in Burton et al. (*Plant Physiol* 134: 224-236, 2004).

Those skilled in the art will appreciate that the invention described herein is susceptible to variations and modifications other than those specifically described. It is to be understood that the invention includes all such variations and modifications. The invention also includes all of the steps, features, compositions and compounds referred to, or indicated in this specification, individually or collectively, and any and all combinations of any two or more of the steps or features.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Also, it must be noted that, as used herein, the singular forms "a", "an" and "the" include plural aspects unless the context already dictates otherwise.

The claims defining the invention are as follows:

1. A method for effecting drought responsive expression of a nucleotide sequence of interest in a wheat plant, the method comprising expressing the nucleotide sequence of interest in cells of the plant, wherein the nucleotide sequence of interest is operably connected to a transcriptional control sequence which is drought inducible in the plant and has no detectable expression in the plant in the absence of drought, and wherein the transcriptional control sequence comprises the nucleotide sequence set forth in SEQ ID NO: 1.

2. The method of claim 1 wherein the nucleotide sequence of interest encodes a DREB polypeptide.

3. The method of claim 2 wherein the DREB polypeptide is a TaDREB3-like polypeptide, or a TaDREB2-like polypeptide.

4. A method for improving the drought tolerance of a wheat plant, the method comprising expressing a nucleotide sequence of interest that improves drought tolerance in cells of the plant according to the method of claim 1, wherein the drought tolerance of the plant is improved in comparison to a plant not expressing the nucleotide sequence of interest.

5. A genetically modified wheat cell comprising:
   (i) a nucleic acid construct comprising the nucleotide sequence set forth in SEQ ID NO: 1 operably linked to a nucleotide sequence of interest; or
   (ii) a genomically integrated form of the nucleic acid construct of (i).

6. A multicellular structure comprising more than one wheat cell of claim 5.

7. The multicellular structure of claim 6, wherein the multicellular structure comprises a wheat plant or a part, organ or tissue thereof.

8. The multicellular structure of claim 7 wherein the nucleotide sequence of interest is expressed in cells of the plant or a part, organ or tissue thereof in response to drought.

9. The multicellular structure of claim 7, wherein the wheat plant or a part, organ or tissue thereof comprises improved tolerance relative to a wheat plant or a part, organ or tissue thereof which does not comprise genetically modified cells that comprise the nucleotide sequence of interest operably connected to the transcriptional control sequence which is drought inducible in a wheat plant and has not detectable expression in the plant in the absence of drought, wherein the transcriptional control sequence comprises the nucleotide sequence set forth in SEQ ID NO: 1.

10. The method of claim 1, further comprising:
    (i) transforming a wheat plant cell with a construct comprising the nucleotide sequence of interest operably connected to the transcriptional control sequence; and
    (ii) generating a transgenic wheat plant from the transformed cells.

11. The method of claim 4, further comprising:
    (i) transforming a wheat plant cell with a construct comprising the nucleotide sequence of interest operably connected to the transcriptional control sequence; and
    (ii) generating a transgenic wheat plant from the transformed cells.

12. The method of claim 4, wherein the nucleotide sequence of interest that improves drought tolerance comprises a nucleotide sequence encoding a DREB factor, a MYC factor, a MYB factor, a HDZip factor, a bZip factor, an HSE factor, an ERF factor, a WRKY factor, a SAPK, a receptor kinase, a MAP kinase, ZmPP2C, type 1 inositol 5-phosphatase, a late embryogenesis abundant (LEA) gene, a dehydrin (DHN) gene, a cold responsive (COR) gene, RD an aquaporin, a PIP, a TIP, a NIP, AtMRP4, an ABCC-type ABC transporter, a NFYA5 TF, NAC, MYB TF, trehalose-6-phosphate synthase (TPS), trehalose-6-phosphate phosphatase (TPP), ABA2, or senescence associated receptor protein kinase (SARK).

* * * * *

SEQUENCE LISTING

<160> NUMBER OF SEQ ID NOS: 3

<210> SEQ ID NO 1
<211> LENGTH: 628
<212> TYPE: DNA
<213> ORGANISM: Zea mays

<400> SEQUENCE: 1

| | | | | | |
|---|---|---|---|---|---|
| cttgacggcc | cgggctggta | tttcaaaact | atagtatttt | aaaattgcat | taacaaacat | 60 |
| gtcctaattg | gtactcctga | gatactatac | cctcctgttt | taaaatagtt | ggcattatcg | 120 |
| aattatcatt | ttacttttta | atgttttctc | ttcttttaat | atattttatg | aattttaatg | 180 |
| tattttaaaa | tgttatgcag | ttcgctctgg | acttttctgc | tgcgcctaca | cttgggtgta | 240 |
| ctgggcctaa | attcagcctg | accgaccgcc | tgcattgaat | aatggatgag | caccggtaaa | 300 |
| atccgcgtac | ccaactttcg | agaagaaccg | agacgtggcg | ggccgggcca | ccgacgcacg | 360 |
| gcaccagcga | ctgcacacgt | cccgccggcg | tacgtgtacg | tgctgttccc | tcactggccg | 420 |
| cccaatccac | tcatgcatgc | ccacgtacac | ccctgccgtg | gcgcgcccag | atcctaatcc | 480 |
| tttcgccgtt | ctgcacttct | gctgcctata | aatggcggca | tcgaccgtca | cctgcttcac | 540 |
| caccggcgag | ccacatcgag | aacacgatcg | agcacacaag | cacgaagact | cgtttaggag | 600 |
| aaaccacaaa | ccaccaagcc | gtgcaagc | | | | 628 |

<210> SEQ ID NO 2
<211> LENGTH: 1004
<212> TYPE: DNA
<213> ORGANISM: Triticum aestivum

<400> SEQUENCE: 2

| | | | | | |
|---|---|---|---|---|---|
| accatacaaa | cctcgatcac | aagccaacac | cattgctact | tgctacggac | aagcgagcga | 60 |
| gctgcggaca | agcgaatcga | gcggtcgata | ccttgcaaga | tggaacagtg | cggcgtgggc | 120 |
| ctctacggcg | tcgtcgaggg | cagcggatac | gcgacggtga | ctaccgcgcc | gcctaagcgg | 180 |
| ccggcggggc | ggaccaagtt | ccgggagacg | cgccacccgc | tctaccgcgg | cgtgcgccgg | 240 |
| cgcggcgccg | cggggcggtg | ggtgtgcgag | gtgcgccagc | ccaacaagaa | gtcgcgcatc | 300 |
| tggctcggca | ccttcgccac | gcccgaggcc | gccgcgcgcg | cccacgacgt | cgccgcgctc | 360 |
| gcgctccggg | gccgagccgc | ctgcctcaac | ttcgccgact | cggccacgct | tctcgccgtc | 420 |
| gaccccgcca | cgctccgcac | gccccatgac | atccgcgccg | ccgcaatcgc | gctcgcccag | 480 |
| gcggcctgcc | cgcacgacgc | gaggaggtcc | tctgtgtccg | tggcgtccgc | gcgggcgccc | 540 |
| gcgatggtga | tcatggagga | ggccgcggcg | gcaccgtacg | acagctacgc | catgtacggc | 600 |
| ggcttggcgg | acctggacca | gcattcctac | tgctactcca | acgggatgag | cggcggcggc | 660 |
| gactggcaga | gtatctcgca | tatggacgga | gccgacgaag | acggcagcta | cggcgcagga | 720 |
| gacgtcgcgc | tctggagcta | ctggtcgcgt | gggatcgatc | gggcagattg | ttgagctcga | 780 |
| ttcgcttgct | cctcagtcct | ccgaaatcga | cgatcgatca | gggaggtcag | cctgagctcg | 840 |
| gaggggagtg | tcgtgcggat | gcacccggca | cgccatatac | tctgctttcc | ctgttcttgg | 900 |
| aaagtggcgc | taaaactgca | cactacagct | tgtcaggaaa | gatgcgcaac | ccagtttgct | 960 |
| gagtggttac | aaacaatcta | aacatcactt | ttcacctttg | taaa | | 1004 |

<210> SEQ ID NO 3
<211> LENGTH: 1043
<212> TYPE: DNA
<213> ORGANISM: Triticum aestivum

```
<400> SEQUENCE: 3
ctctgcttgc tcgcagtaac tcgagtccta ctccctgcac ggtcctccca ttaccacgag      60
cgagcgcgtg tcatctcata cgggcacgcg gggctacgtg gtgctctctg cgcgcacatg     120
gcggcgagcg agcagagctc cgagtcctcg tcgacgtcct gcacttcctc ctactccacg     180
tcctcgtgct cccccagggc cgacgacaag aagcggaacg gcggcggcaa gcggaagcgc     240
gcagcggcgg ccgacgagga gccggccccg gcggcggcgg cggcgtcgta tcgcggcgtg     300
cggatgcggg cgtggggcaa gtgggtgtcg gagatcaggg agccgcgcaa gaagtcccgc     360
atctggctcg gcaccttccc gtgcccgag atggccgcgc gcgcccacga cgccgccgcg     420
ctcagcatca agggcgcccg cgccgtgctt aacttcccgg acctcgcgcc cgcgctccct     480
cgcccggcct ccctcgcccc gtgcgacgtc caggccgccg ccgcgcgcgc cgccctcatg     540
cacgaccacg accaccagtg ctgctccgcc tcaacctccc ccgccgccgc gccggactcc     600
gcgcgcggca atgccccggc gccatgcgac cagccgccg cgcgagacga gccggagcat     660
gagccgccgt tccagccgag ccagggaaat gagcagcagc tcacggctgc acaggtggag     720
atggtgttcg acgagctggc gccgctgtgg gtggagaacg tggtggattt cgcgccgtcc     780
gatcactgct ggacggcgta cgattgtctc gacccaatcg gcttccagcc tctcctgtgg     840
gagtattagg cttggcgtac aacaccttga tttccttct tcttcttttc ttggttttg      900 tgtggttttc tagtgctgct taaaatgaag cacattttc gctttgtcat ttggtttgcg    960
tttgcgcatg cttgggtttg gactacttgt aagttgagat gtttgtgacc aatttagctt   1020
agatgtgagt tgagtttgaa caa                                            1043
```